(12) United States Patent
Etzkorn et al.

(10) Patent No.: US 9,332,935 B2
(45) Date of Patent: May 10, 2016

(54) DEVICE HAVING EMBEDDED ANTENNA

(71) Applicant: Verily Life Sciences LLC, Mountain View, CA (US)

(72) Inventors: James Etzkorn, Mountain View, CA (US); Stephen O'Driscoll, San Francisco, CA (US)

(73) Assignee: Verily Life Sciences LLC, Mountain View, CA (US)

(*) Notice: Subject to any disclaimer, the term of this patent is extended or adjusted under 35 U.S.C. 154(b) by 0 days.

(21) Appl. No.: 14/035,352

(22) Filed: Sep. 24, 2013

(65) Prior Publication Data

US 2014/0371559 A1 Dec. 18, 2014

Related U.S. Application Data

(63) Continuation of application No. 13/918,522, filed on Jun. 14, 2013.

(51) Int. Cl.
*A61B 5/00* (2006.01)
*A61B 5/145* (2006.01)
(Continued)

(52) U.S. Cl.
CPC .............. *A61B 5/14532* (2013.01); *A61B 5/002* (2013.01); *A61B 5/682* (2013.01);
(Continued)

(58) Field of Classification Search
CPC .............. A61B 5/1455; A61B 5/14551; A61B 5/14532; A61B 5/002; A61B 5/145; A61B 5/682; A61B 5/1486; A61B 5/6821
USPC ......... 600/309, 310, 316, 318–320, 322, 323, 600/340, 341, 344, 345, 347, 356, 365, 373, 600/473, 476, 372, 382, 383; 343/700, 742, 343/748
See application file for complete search history.

(56) References Cited

U.S. PATENT DOCUMENTS 3,958,560 A  5/1976  March
4,014,321 A  3/1977  March
(Continued)

FOREIGN PATENT DOCUMENTS

EP   0369942   5/1990
EP   0686372   12/1995
(Continued)

OTHER PUBLICATIONS

Happich, "Medical contact lens embedds wireless MEMs sensor", Mar. 25, 2010; http://www.electronics-eetimes.com/en/medical-contact-lens-embedds-wireless-mems-sensor.html?cmp_id=7 &news_id=222901145.*
(Continued)

*Primary Examiner* — Eric Winakur
*Assistant Examiner* — Chu Chuan (JJ) Liu
(74) *Attorney, Agent, or Firm* — McDonnel Boehnen Hulbert & Berghoff LLP

(57) ABSTRACT

Body-mountable devices and methods for embedding a structure in a body-mountable device are described. A body-mountable device includes a transparent polymer and a structure embedded in the transparent polymer. The transparent polymer defines a posterior side and an anterior side of the body-mountable device. The structure has an outer diameter and an inner diameter and includes a sensor configured to detect an analyte and an antenna. The antenna includes a plurality of conductive loops spaced apart from each other between the outer diameter and the inner diameter.

16 Claims, 12 Drawing Sheets

(51) Int. Cl.
*G02C 7/04* (2006.01)
*A61B 5/1486* (2006.01)

(52) U.S. Cl.
CPC .............. *A61B 5/6821* (2013.01); *G02C 7/04* (2013.01); *A61B 5/1486* (2013.01); *A61B 2562/12* (2013.01); *Y10T 156/1028* (2015.01)

(56) References Cited

U.S. PATENT DOCUMENTS

| | | |
|---|---|---|
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,979,516 A | 12/1990 | Abraham |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,217,015 A * | 6/1993 | Kaye et al. .................. 600/405 |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,646,633 A * | 7/1997 | Dahlberg ............... 343/700 MS |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,300,914 B1 * | 10/2001 | Yang ....................... 343/741 |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 6,982,058 B2 | 1/2006 | Jacobson |
| 6,992,630 B2 * | 1/2006 | Parsche .................. 343/732 |
| 7,018,040 B2 | 3/2006 | Blum et al. |
| 7,131,945 B2 | 11/2006 | Fink et al. |
| 7,169,106 B2 | 1/2007 | Fleischman et al. |
| 7,308,317 B1 | 12/2007 | Okandan et al. |
| 7,398,119 B2 | 7/2008 | Lambert et al. |
| 7,403,805 B2 * | 7/2008 | Abreu .................... 600/318 |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,901,706 B2 | 3/2011 | Lally et al. |
| 7,907,931 B2 | 3/2011 | Hartigan et al. |
| 7,910,934 B2 | 3/2011 | Kim et al. |
| 7,926,940 B2 | 4/2011 | Blum et al. |
| 7,927,519 B2 | 4/2011 | Domschke et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,131,333 B2 | 3/2012 | Chapoy et al. |
| 8,142,016 B2 | 3/2012 | Legerton et al. |
| 8,224,415 B2 | 7/2012 | Budiman |
| 8,241,574 B2 | 8/2012 | Burles et al. |
| 8,258,635 B2 | 9/2012 | Greenburg et al. |
| 8,385,998 B2 | 2/2013 | Zhang et al. |
| 8,425,759 B2 | 4/2013 | Wilsey |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2004/0186366 A1 | 9/2004 | Leonardi et al. |
| 2005/0045589 A1 | 3/2005 | Rastogi et al. |
| 2005/0221276 A1 | 10/2005 | Rozakis et al. |
| 2006/0183986 A1 | 8/2006 | Rice et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |

(56) References Cited

U.S. PATENT DOCUMENTS

| | | | |
|---|---|---|---|
| 2010/0016704 | A1 | 1/2010 | Naber et al. |
| 2010/0028559 | A1 | 2/2010 | Yan et al. |
| 2010/0072643 | A1 | 3/2010 | Pugh et al. |
| 2010/0109175 | A1 | 5/2010 | Pugh et al. |
| 2010/0110372 | A1 | 5/2010 | Pugh et al. |
| 2010/0113901 | A1 | 5/2010 | Zhang et al. |
| 2010/0133510 | A1 | 6/2010 | Kim et al. |
| 2010/0249548 | A1 | 9/2010 | Muller |
| 2010/0265680 | A1 | 10/2010 | Tai et al. |
| 2010/0297016 | A1 | 11/2010 | Geddes et al. |
| 2011/0015512 | A1 | 1/2011 | Pan et al. |
| 2011/0028807 | A1 | 2/2011 | Abreu |
| 2011/0040161 | A1 | 2/2011 | Abreu |
| 2011/0055317 | A1 | 3/2011 | Vonog et al. |
| 2011/0063568 | A1 | 3/2011 | Meng et al. |
| 2011/0084834 | A1 | 4/2011 | Sabeta |
| 2011/0116035 | A1 | 5/2011 | Fritsch et al. |
| 2011/0157541 | A1 | 6/2011 | Peyman |
| 2011/0157544 | A1 | 6/2011 | Pugh et al. |
| 2011/0184271 | A1 | 7/2011 | Veciana et al. |
| 2011/0274680 | A1 | 11/2011 | Mazed et al. |
| 2011/0286064 | A1 | 11/2011 | Burles et al. |
| 2011/0298794 | A1 | 12/2011 | Freedman |
| 2012/0026458 | A1 | 2/2012 | Qiu et al. |
| 2012/0038881 | A1 | 2/2012 | Amirparviz et al. |
| 2012/0041287 | A1 | 2/2012 | Goodall et al. |
| 2012/0041552 | A1 | 2/2012 | Chuck et al. |
| 2012/0069254 | A1 | 3/2012 | Burton |
| 2012/0075168 | A1 | 3/2012 | Osterhout et al. |
| 2012/0075574 | A1 | 3/2012 | Pugh et al. |
| 2012/0078071 | A1 | 3/2012 | Bohm et al. |
| 2012/0088258 | A1 | 4/2012 | Bishop et al. |
| 2012/0092612 | A1 | 4/2012 | Binder et al. |
| 2012/0109296 | A1 | 5/2012 | Fan |
| 2012/0177576 | A1 | 7/2012 | Hu |
| 2012/0201755 | A1 | 8/2012 | Rozakis et al. |
| 2012/0206691 | A1 | 8/2012 | Iwai |
| 2012/0245444 | A1 | 9/2012 | Otis et al. |
| 2012/0259188 | A1 | 10/2012 | Besling |
| 2012/0310151 | A1 | 12/2012 | Takahata et al. |
| 2013/0194540 | A1* | 8/2013 | Pugh et al. ............ 351/159.03 |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | WO 2012/013353 | 2/2012 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Bionic contact lens 'to project emails before eyes,' http://www.kurzweilai.netforums/topic/bionic-contact-lens-to-project-emails-before-eyes, Last accessed Mar. 14, 2012, 2 pages.

Brahim, et al., "Polypyrrole-hydrogel composites for the construction of clinically important biosensors," 2002, Biosensors & Bioelectronics, pp. 53-59, vol. 17.

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi edu/seke/dms11/DMS/2_{Kohji}_Mitsubayashi.pdf, Last accessed Jul. 27, 2012, 4 pages.

"Contact Lenses: Look Into My Eyes," The Economist, Jun. 2, 2011, http://www.economist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3-µW CMOS Glucose Sensor for Wireless Contact-Lens Tear Glucose Monitoring ," IEEE Journal of Solid-State Circuits, Jan. 2012, pp. 335-344, vol. 47, No. 1.

Liao, et al., "A 3-µW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.

Lingley, et al., "Multipurpose integrated active contact lenses," SPIE, 2009, 2 pages.

Liu, et al., "Miniature Amperometric Self-Powered Continuous Glucose Sensor with Linear Response," Analytical Chemistry, 2012, 7 pages.

Loncar, et al., "Design and Fabrication of Silicon Photonic Crystal Optical Waveguides," Journal of Lightwave Technology, Oct. 2000, pp. 1402-1411, vol. 18, No. 10.

Murdan, "Electro-responsive drug delivery from hydrogels," Journal of Controlled Release, 2003, pp. 1-17, vol. 92.

Pandey, et al., "A Fully Integrated RF-Powered Contact Lens With a Single Element Display," IEEE Transactions on Biomedical Circuits and Systems, Dec. 2010, pp. 454-461, vol. 4, No. 6.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Selner, et al., "Novel Contact Lens Electrode Array for Multi-electrode Electroretinography (meERG)," IEEE, 2011, 2 pages.

Singh , et al., "Novel Approaches in Formulation and Drug Delivery using Contact Lenses," Journal of Basic and Clinical Pharmacy, May 2011, pp. 87-101, vol. 2, Issue 2.

Thomas, et al., "Functional Contact Lenses for Remote Health Monitoring in Developing Countries," IEEE Global Humanitarian Technology Conference, 2011, pp. 212-217, IEEE Computer Society.

Tweedie, et al., "Contact creep compliance of viscoelastic materials via nanoindentation," J. Mater. Res., Jun. 2006, pp. 1576-1589, vol. 21, No. 2, Materials Research Society.

Wall, K., "Active contact lens that lets you see like the Terminator patented," Feb. 10, 2012, http://vvww.patexia.com/feed/active-contact-lens-that-lets-you-see-like-the-terminator-patented-2407, Last accessed Mar. 28, 2012, 5 pages.

(56) References Cited

OTHER PUBLICATIONS

Zarbin, et al., "Nanotechnology in ophthalmology," Can J Ophthalmol, 2010, pp. 457-476, vol. 45, No. 5.
Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
Ho et al., "Contact Lens With Integrated Inorganic Semiconductor Devices," MEMS 2008. IEEE 21st International Conference on. IEEE, 2008., pp. 403-406.
Kudo et al., "A flexible and wearable glucose sensor based on functional polymers with Soft-MEMS techniques," Biosensors and Bioelectronics, 2006, vol. 22, pp. 558-562.
Lähdesmäki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Parviz, Babak A., "For Your Eyes Only," IEEE Spectrum, Sep. 2009, pp. 36-41.
Patel et al., "Flexible Glucose Sensor Utilizing Multilayer PDMS Process," Engineering in Medicine and Biology Society, 2008. EMBS 2008 30th Annual International Conference on the IEEE, pp. 5749-5752.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.
Stauth et al., "Self-assembled single-crystal silicon circuits on plastic," PNAS, Sep. 19, 2006, pp. 13922-13927, vol. 103, No. 38.
Yao, H. et al., "A contact lens with integrated telecommunication circuit and sensors for wireless and continuous tear glucose monitoring," J. Micromech. Microeng., 2012, pp. 1-10, vol. 22.
Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.
Yao et al., "A contact lens with embedded sensor for monitoring tear glucose level," Biosensors and Bioelectronics, 2011, pp. 3290-3296, vol. 26.
Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.
Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.
Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.
Zhang et al., "Microfabrication and Applications of Opto-Microfluidic Sensors," Sensors, 2011, vol. 11, pp. 5360-5382.
International Search Report and Written Opinion prepared by the Korean Patent Office in International Patent Application Serial No. PCT/US2014/042152, mailed Oct. 12, 2014.
Mohan et al. "Design of fully integrated wireless CMOS MEMS device for intraocular pressure measurement", A thesis submitted to the Graduate Faculty of North Carolina State University in partial fulfillment of the requirements for the degree of Masters of Science, May 10, 2008, retrieve:http://www.lib.ncsu.edu/resolver/1840.16/631/1/etd.pdf.

* cited by examiner

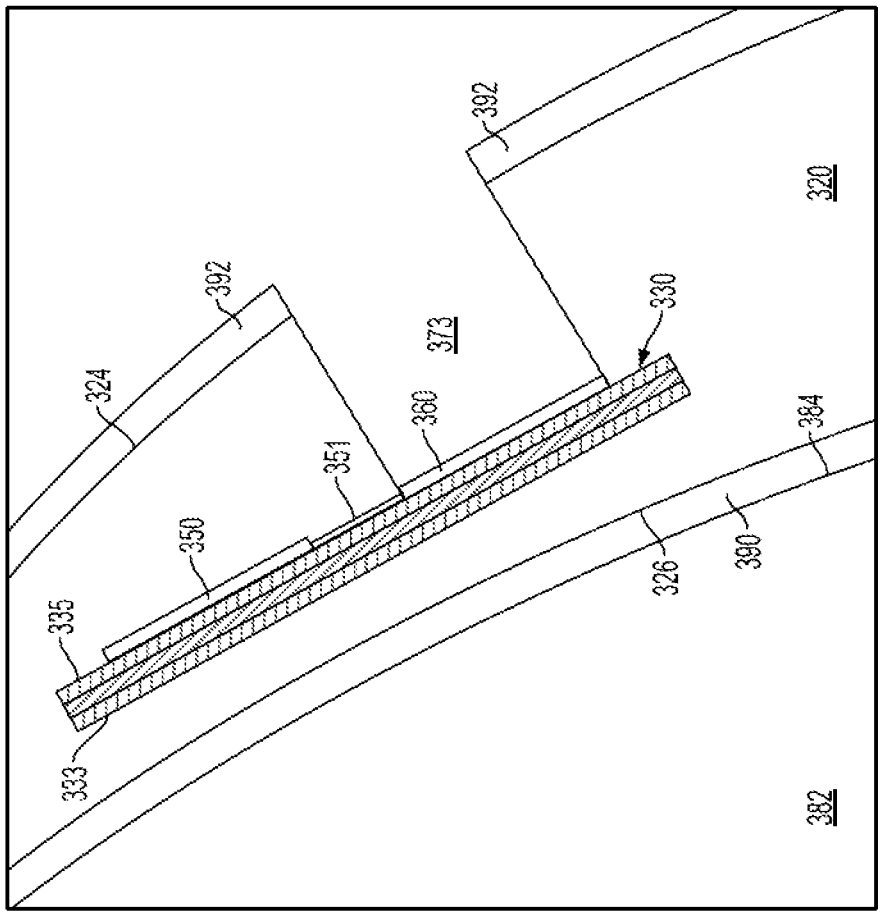
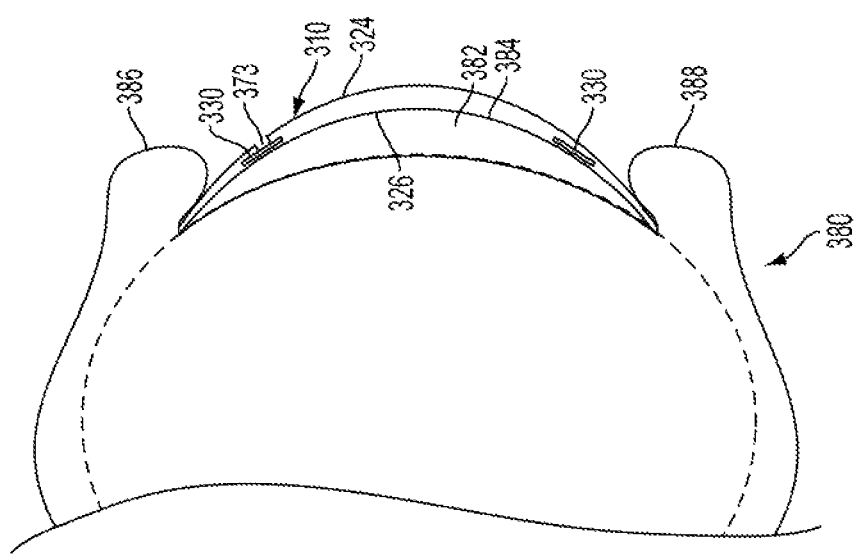
FIG. 3d
FIG. 3c

DEVICE HAVING EMBEDDED ANTENNA

CROSS REFERENCE TO RELATED APPLICATIONS

The present application is a continuation of U.S. Patent Application No. 13/918,522, filed Jun. 14, 2013, which is currently pending. The entire disclosure contents of this application are herewith incorporated by reference into the present application.

BACKGROUND

Unless otherwise indicated herein, the materials described in this section are not prior art to the claims in this application and are not admitted to be prior art by inclusion in this section.

A body-mountable device may be configured to monitor health-related information based on at least one analyte detected in a fluid of a user wearing the body-mountable device. For example, the body-mountable device may comprise an eye-mountable device that may be in the form of a contact lens that includes a sensor configured to detect the at least one analyte (e.g., glucose) in a tear film of a user wearing the eye-mountable device. The body-mountable device may also be configured to monitor various other types of health-related information.

SUMMARY

In one aspect, a body-mountable device is disclosed. An example body-mountable device includes: a transparent polymer, wherein the transparent polymer defines a posterior side and an anterior side of the body-mountable device; and a structure embedded in the transparent polymer, wherein the structure has an outer diameter and an inner diameter and includes a sensor configured to detect an analyte and an antenna, wherein the antenna includes a plurality of conductive loops spaced apart from each other between the outer diameter and the inner diameter.

In another aspect, a method involves: forming a first polymer layer, such that the first polymer layer has a curvature, wherein the first polymer layer defines a posterior side of a body-mountable device; positioning a structure on the first polymer layer, wherein the structure has an outer diameter and an inner diameter and includes a sensor configured to detect an analyte and an antenna, and wherein the antenna includes a plurality of conductive loops spaced apart from each other between the outer diameter and the inner diameter; conforming the structure positioned on the first polymer layer to the curvature of the first polymer layer; and forming a second polymer layer over the first polymer layer and the structure, such that the structure is fully enclosed by the first polymer layer and the second polymer layer, wherein the second polymer layer defines an anterior side of the body-mountable device.

In yet another aspect, a system is disclosed. A system includes means for forming a first polymer layer, such that the first polymer layer has a curvature, wherein the first polymer layer defines a posterior side of a body-mountable device; means for positioning a structure on the first polymer layer, wherein the structure has an outer diameter and an inner diameter and includes a sensor configured to detect an analyte and an antenna, and wherein the antenna includes a plurality of conductive loops spaced apart from each other between the outer diameter and the inner diameter; means for conforming the structure positioned on the first polymer layer to the curvature of the first polymer layer; and means for forming a second polymer layer over the first polymer layer and the structure, such that the structure is fully enclosed by the first polymer layer and the second polymer layer, wherein the second polymer layer defines an anterior side of the body-mountable device.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 3c is a side cross-section view of the eye-mountable device shown in FIG. 3a while mounted to a corneal surface of an eye, according to an example embodiment.

FIG. 3d is a side cross-section view showing tear film layers surrounding the surfaces of the eye-mountable device mounted as shown in FIG. 3c, according to an example embodiment.

DETAILED DESCRIPTION

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. It will be readily understood that certain aspects of the disclosed systems and methods can be arranged and combined in a wide variety of different configurations, all of which are contemplated herein.

I. Introduction

A body-mountable device may include a transparent polymer and a structure embedded in the transparent polymer that has an outer diameter and an inner diameter. The transparent polymer defines a posterior side and an anterior side of the body-mountable device. The structure includes a sensor configured to detect an analyte and an antenna that includes a plurality of conductive loops spaced apart from each other between the outer diameter and the inner diameter. Beneficially, the plurality of conductive loops can reduce buckling of the structure (e.g., one or more protrusions from a surface of the structure) when it is bent to conform to a curvature of the transparent polymer.

As used throughout this disclosure, the anterior side of the body-mountable device refers to an outward-facing side of the body-mountable device, whereas the posterior side of the body-mountable device refers to an inward-facing side of the body-mountable device. In particular, when the body-mountable device comprises an eye-mountable device and the eye-mountable device is mounted on an eye of the user, the anterior side corresponds to a side of the eye-mountable device that is facing outward and thus not touching the eye of the user. Further, when the eye-mountable device is mounted on an eye of the user, the posterior side corresponds to a side of the eye-mountable device that is facing inward and thus touching the eye of the user.

II. Example Systems And Devices

A body-mountable device may be configured to monitor health-related information based on at least one analyte detected in a fluid of a user wearing the body-mountable device. An example body-mountable device that comprises an eye-mountable device that is configured to detect the at least one analyte in a tear film of a user wearing the eye-mountable device will now be described in greater detail.

Figure 1:
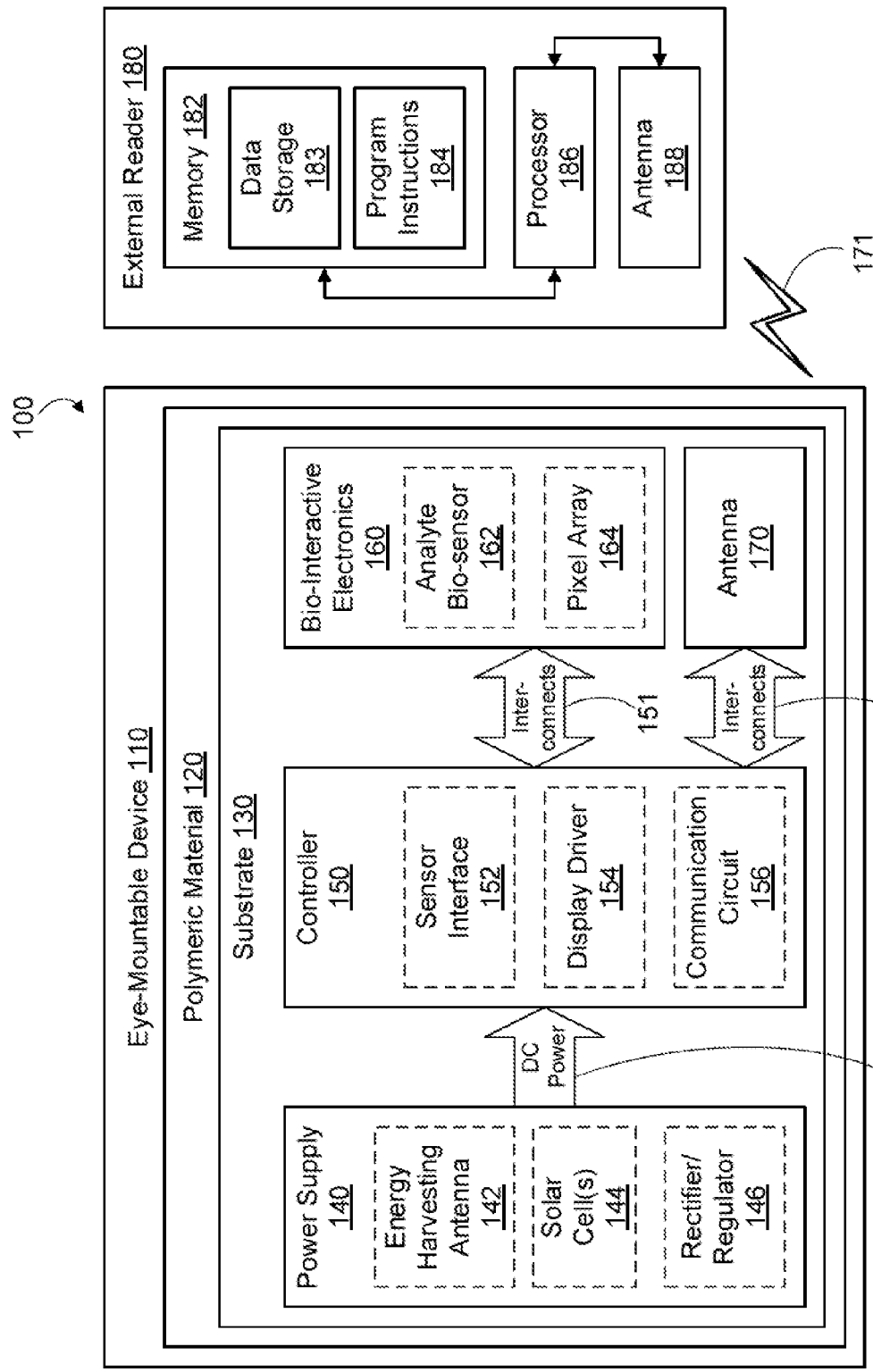
FIG. 1 is a block diagram of a system that includes an eye-mountable device in wireless communication with an external reader, according to an example embodiment.

FIG. 1 is a block diagram of a system 100 with an eye-mountable device 110 in wireless communication with an external reader 180, according to an example embodiment. The exposed regions of the eye-mountable device 110 are made of a polymeric material 120 formed to be contact-mounted to a corneal surface of an eye. In accordance with exemplary methods, the polymeric material 120 may comprise a first polymer layer and a second polymer layer.

Substrate 130 is embedded in the polymeric material 120 to provide a mounting surface for a power supply 140, a controller 150, bio-interactive electronics 160, and an antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it may also be referred to as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the anterior or outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more bio-compatible materials, such as those employed for use in contact lenses or other ophthalmic applications involving direct contact with the corneal surface. The polymeric material 120 can optionally be formed in part from such bio-compatible materials or can include an outer coating with such bio-compatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of resists, masks, and deposition techniques can be employed to pattern materials on the substrate 130.

The substrate 130 can be a relatively rigid polymeric material, such as polyethylene terephthalate ("PET"), paralyene, or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from a center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in a center region of the eye-mountable device 110. The bio-interactive electronics 160 and/or the substrate 130 can be substantially transparent to incoming visible light to mitigate interference with light transmission to the eye. Moreover, in some embodiments, the bio-interactive electronics 160 can include a pixel array 164 that emits and/or transmits light to be perceived by the eye according to display driver instructions. Thus, the bio-interactive electronics 160 can optionally be positioned in the center of the eye-mountable device so as to generate perceivable visual cues to a wearer of the eye-mountable device 110, such as by displaying information via the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a 1 centimeter diameter, a radial thickness of approximately 1 millimeter, and a thickness of about 50 micrometers. The substrate 130 can optionally be aligned with the curvature of the anterior side of the eye-mountable device 110.

The power supply 140 is configured to harvest ambient energy to power the controller 150 and the bio-interactive electronics 160. For example, a radio-frequency energy harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system (not shown) can be included to capture energy from ambient vibrations. The energy-harvesting antenna 142 can optionally be a dual-purpose antenna that is also used to communicate information to the external reader 180. That is, the functions of the antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the energy harvesting antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices arranged to mitigate high frequency variations in the ambient energy harvesting antenna 142 and/or solar cell(s) 144. For example, an energy storage device (e.g., capacitor, inductor, etc.) can be connected to the output of the rectifier/regulator 146 so as to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such as an analyte bio-sensor 162, in bio-interactive electronics 160 to obtain input from the biological environment. Alternatively or additionally, the interaction could involve the use of one or more components, such as the pixel array 164, to provide an output to the biological environment.

In one example, a sensor interface module 152 can be included for operating the analyte bio-sensor 162. The analyte bio-sensor 162 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 152 can be a potentiostat configured to apply a voltage difference between the working and reference electrodes while measuring a current through the working electrode.

In some embodiments, at least a portion of the bio-interactive electronics 160, the controller 150, the power supply, and/or the antenna 170 can be embedded in the substrate 130. And, in some embodiments, at least a portion of the bio-interactive electronics 160 (e.g., the analyte bio-sensor 162) can be surrounded by the substrate 130, except for a surface of the at least a portion of the bio-interactive electronics 160 being exposed by an opening in the substrate 130.

In some instances, a reagent can also be included to sensitize the electrochemical sensor to desired analytes. For example, a layer of glucose oxidase ("GOD") can be situated around the working electrode to catalyze glucose into hydrogen peroxide ($H_2O_2$). The hydrogen peroxide can then be oxidized at the working electrode, which releases electrons to the working electrode, which generates a current.

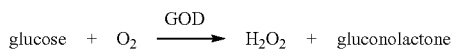

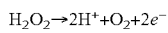

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules flow and/or diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the external reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the antenna 170 can be implemented with the same physical antenna. For example, a loop antenna can both harvest incident radiation for power generation and communicate information via backscatter radiation.

The external reader 180 includes an antenna 188 (or group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g., RAM) or non-volatile (e.g., ROM) storage system readable by the processor 186. The memory 182 can include a data storage 183 to store indications of data substrates, such as sensor readings (e.g., from the analyte bio-sensor 162), program settings (e.g., to adjust behavior of the eye-mountable device 110 and/or external reader 180), etc. The memory can also include program instructions 184 for execution by the processor 186 to cause the external reader to perform processes specified by the program instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged into a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earing, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the substrate of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the antenna 170) are rectified and/or regulated in the rectifier/regulator 146 and a regulated DC supply voltage 647 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162 sufficient to cause the analyte to undergo an electrochemical reaction at the working electrode. The current through the working electrode can be measured to provide the sensor output indicative of the analyte concentration. The controller 150 can operate the antenna 170 to communicate the sensor results back to the external reader 180 (e.g., via the communication circuit 156). The sensor result can be communicated by, for example, modulating an impedance of the antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the on-board controller 150 and the bio-interactive electronics 160. For example, radio frequency radiation 171 can be supplied to power the eye-mountable device 110 long enough to carry out a tear film analyte concentration measurement and communicate the results. For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Figure 2A:
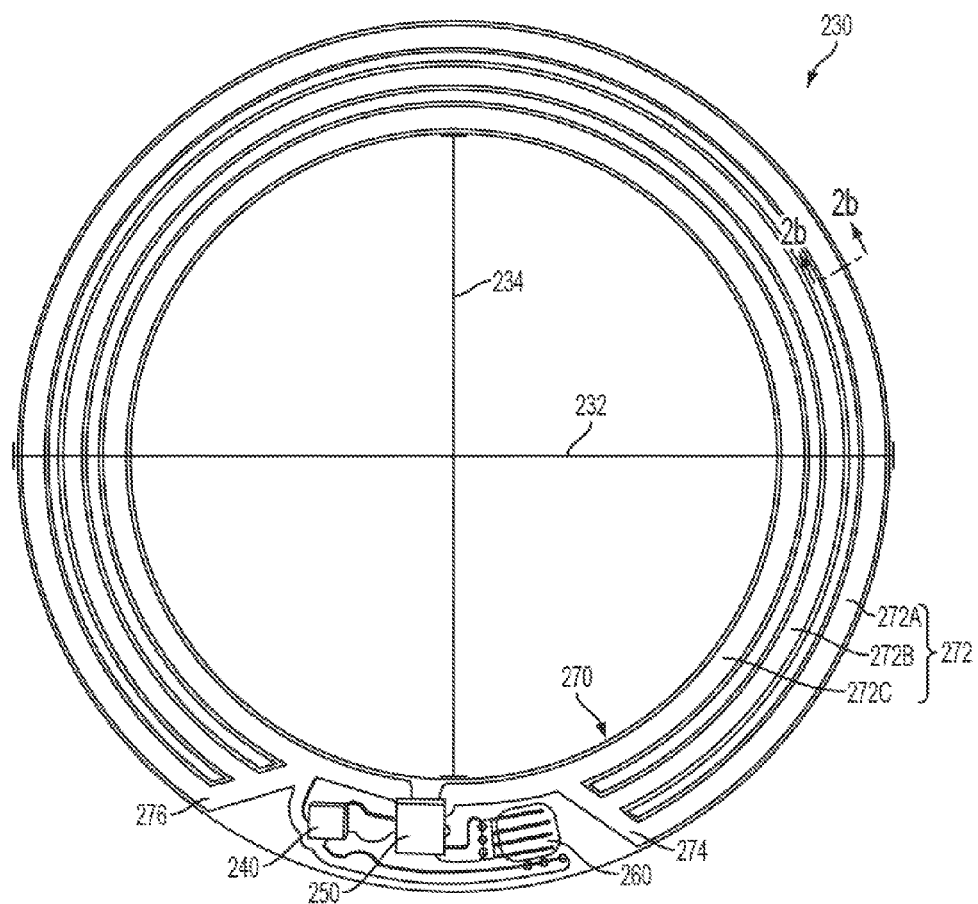
FIG. 2a is a top view of a structure, according to an example embodiment.

FIG. 2a is a top view of a structure 230, according to an example embodiment. In particular, the structure 230 has an outer diameter 232 and an inner diameter 234 and includes electronics 240, electronics 250, a sensor 260, and an antenna 270 disposed thereon. The structure 230 may take the form of or be similar in form to the substrate 130.

The structure 230 can have various sizes. For instance, the size of the structure 230 may depend on which analyte an eye-mountable device is configured to detect. In an example, the structure 230 has a maximum height of approximately 50 between 150 micrometers. Of course, other maximum heights of the structure 230 are possible as well.

In an example, the structure 230 has a height dimension of at least 50 micrometers. In other words, at some point of the structure 230, the height of the structure 230 may be at least 50 micrometers. In an example, this height dimension may correspond to a maximum height of the structure 230. In accordance with the present disclosure, the maximum height of the structure 230 corresponds to the height of the structure 230 at its highest point. For instance, in the example where the structure 230 comprises the sensor 260 and the electronics 250, the height of the structure 230 may vary (and thus the structure 230 may have various height dimensions). For example, the height of the structure 230 may be higher at a point where the electronics 250 is mounted on the structure 230, whereas the height may be lower at a point where there is no chip on the structure 230. In such an example, the maximum height may correspond to the point where the electronics 250 is mounted on the structure 230.

The outer diameter 232 and the inner diameter 234 could take various different forms in various different embodiments. In some embodiments, the outer diameter can have a length between 12.5 and 15 millimeters. Moreover, in some embodiments, the inner diameter can have a length greater than 8 millimeters. And other lengths of the outer diameter 232 and/or inner diameter 234 are possible as well.

The electronics 240 and 250 could be configured in a variety of ways. For example, the electronics 240 and/or the electronics 250 may be configured to operate the sensor 260 and the antenna 270. And, in such an example, the electronics 240 and/or the electronics 250 may be configured for wireless communication with an external reader, such as the external reader 180. In some embodiments, the electronics 240 and the electronics 250 may provide a bias voltage for the sensor 260 and adjust backscattered radio frequency (RF) that is proportional to a current that is passing through the sensor 260.

The electronics 240 and the electronics 250 could take various different forms in various different embodiments. In some embodiments, the electronics 240 and/or the electronics 250 can comprise a chip including one or more logical elements. The electronics 240 and/or the electronics 250 may take the form of or be similar in form to the controller 150.

The sensor 260 is configured to detect one or more analytes. The sensor 260 could take various different forms in various different embodiments. In some embodiments, the sensor 260 can comprise a pair of electrodes, such as a working electrode and a reference electrode. The sensor 260 may take the form of or be similar in form to the analyte bio-sensor 162.

The antenna 270 is configured for communications and/or harvesting energy as described herein. The antenna 270 includes a plurality of conductive loops 272 spaced apart from each other between the outer diameter 232 and the inner diameter 234. In the illustrated example, the plurality of conductive loops 272 includes three conductive loops 272A, 272B, and 272C. However, in other examples, a plurality of conductive loops may include more than three conductive loops, such as five conductive loops, nine conductive loops, etc.

As shown in FIG. 2a, the conductive loops 272A, 272B, and 272C are connected in parallel. With this arrangement, each of the conductive loops in the plurality of conductive loops 272 is electrically connected to the electronics 240, the electronics 250, and the sensor 260 via a first connection 274 and a second connection 276. And the electronics 240, the electronics 250, and the sensor 260 are electrically connected via the first connection 274 and the second connection 276. The first connection 274 and the second connection 276 may take the form of or be similar in form to the interconnects 151 and 157. Moreover, as shown in FIG. 2a, the conductive loops 272A, 272B, and 272C are substantially concentric. The term "substantially concentric," as used in this disclosure, refers to exactly concentric and/or one or more deviations from exactly concentric that do not significantly impact embedding a structure in a body-mountable device as described herein.

And as shown in FIG. 2a, the conductive loops 272A, 272B, and 272C are spaced apart from each other between the outer diameter 232 and the inner diameter 234. In an example, the conductive loops 272A, 272B, and 272C can be spaced apart from adjacent conductive loops by a distance between 100 to 200 micrometers. Other distances are possible as well.

In some embodiments, one of the conductive loops 272A, 272B, and 272C can have a width of 333 micrometers. Other widths of the conductive loops 272A, 272B, and 272C are possible as well. Moreover, in some embodiments, the conductive loops 272A, 272B, and 272C can each have the same width (e.g., the conductive loops 272A, 272B, and 272C can each have a width of 333 micrometers). However, in some embodiments, the conductive loops 272A, 272B, and 272C might not have the same width.

Figure 2B:
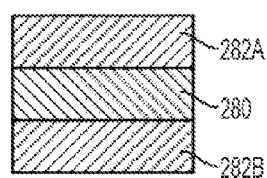
FIG. 2b is a side cross-section view of the structure shown in FIG. 2a, according to an example embodiment.

Each conductive loop in the plurality of conductive loops 272 can comprise a respective metal layer disposed between respective polymer layers. With this arrangement, the polymer layers might block moisture from the metal layer. FIG. 2b is a side cross-section view of the structure shown in FIG. 2a, according to an example embodiment. As shown in FIG. 2b, the conductive loop 272A comprises a metal layer 280 disposed between polymer layers 282A and 282B. The respective metal layers of the conductive loops 272B and 272C may take the form of or be similar in form to the to the metal layer 280, and the respective polymer layers of the conductive loops 272B and 272C may take the form of or be similar in form to the polymer layers 282A and 282B.

In some embodiments, the metal layer 280 can comprise gold or another conductive material that can be deposited on the structure 230, such as platinum, palladium, titanium, carbon, aluminum, copper, silver, and/or silver-chloride. And in at least one such embodiment, the metal layer 280 can have a thickness between 5 and 30 micrometers. Other thicknesses of the metal layer 280 are possible as well. In an example, the metal layer 280 can be formed by a process that includes electroplating.

Moreover, in some embodiments, the polymer layers 282A and 282B can comprise a relatively rigid transparent polymer, such as PET or paralyene. And in at least one such embodiment, the polymer layers 282A and 282B can have a thickness between 10 and 50 micrometers, such as 15 micrometers. Other thicknesses of the polymer layers 282A and 282B are possible as well. In an example, the polymer layers 282A and 282B can be formed by a process that includes chemical vapor deposition.

In an example, the plurality of conductive loops 272 can be formed by a process that includes etching a portion of a metal layer disposed between polymer layers with an inductively coupled plasma, such as an oxygen plasma.

Figure 3A:
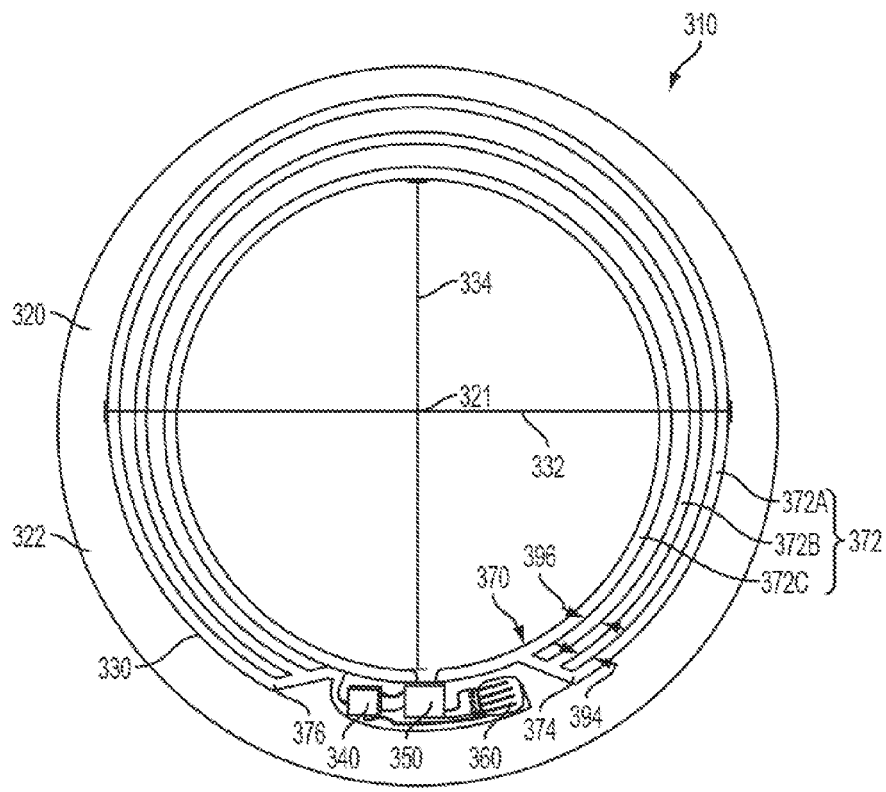
FIG. 3a is a top view of an eye-mountable device, according to an example embodiment.
Figure 3B:
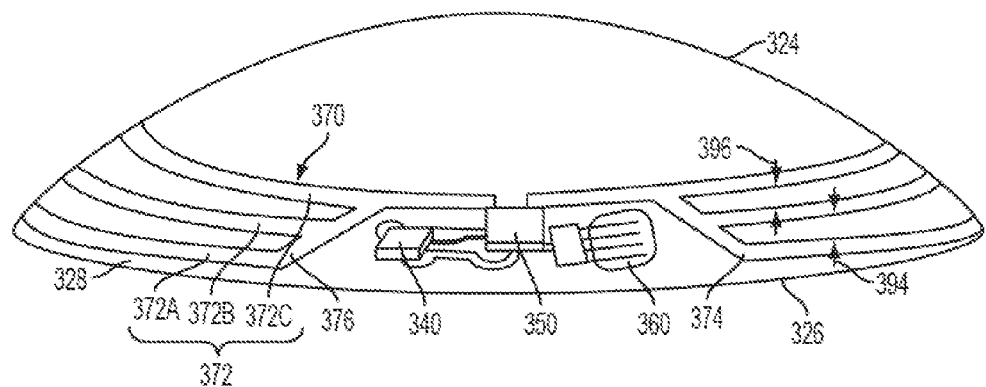
FIG. 3b is a side view of the eye-mountable device shown in FIG. 3a, according to an example embodiment.

FIG. 3*a* is a top view of an eye-mountable electronic device 310. FIG. 3*b* is a side view of the eye-mountable electronic device 310 shown in FIG. 3*a*. It is noted that relative dimensions in FIGS. 3*a* and 3*b* are not necessarily to scale, but have been rendered for purposes of explanation only in describing the arrangement of the eye-mountable electronic device 310. The eye-mountable device 310 is formed of a transparent polymer 320 shaped as a curved disk. The transparent polymer 320 can be a substantially transparent material to allow incident light to be transmitted to the eye while the eye-mountable device 310 is mounted to the eye. The transparent polymer 320 can be a bio-compatible material similar to those employed to form vision correction and/or cosmetic contact lenses in optometry, such as PET, polymethyl methacrylate ("PMMA"), silicone hydrogels, combinations of these, etc. The transparent polymer 320 could take the form of or be similar in form to the polymeric material 120.

The transparent polymer 320 can be formed with one side having a posterior side 326 (i.e., concave surface) suitable to fit over a corneal surface of an eye. The opposing side of the disk can have anterior side 324 (i.e., convex surface) that does not interfere with eyelid motion while the eye-mountable device 310 is mounted to the eye. A circular outer side edge 328 connects the posterior side 326 and anterior side 324.

The eye-mountable device 310 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 310 can be selected according to the size and/or shape of the corneal surface and/or the scleral surface of the wearer's eye.

While the eye-mountable device 310 is mounted in an eye, the anterior side 324 faces outward to the ambient environment while the posterior side 326 faces inward, toward the corneal surface. The anterior side 324 can therefore be considered an outer, top surface of the eye-mountable device 310 whereas the posterior side 326 can be considered an inner, bottom surface. The "top" view shown in FIG. 3*a* is facing the anterior side 324.

The structure 330 is embedded in the transparent polymer 320. The substrate 330 can be embedded to be situated along an outer periphery 322 of the transparent polymer 320, away from a center region 321. The structure 330 does not interfere with vision because it is too close to the eye to be in focus and is positioned away from the center region 321 where incident light is transmitted to the light-sensing portions of the eye. The structure 330 can take the form or be similar in form to the substrate 130 and/or the structure 230.

The structure 330 has an outer diameter 332 and an inner diameter 334 and includes electronics 340, electronics 350, a sensor 360, and an antenna 370 disposed thereon. The outer diameter 332 may take the form of or be similar in form to the outer diameter 232, the inner diameter 334 may take the form of or be similar in form to the inner diameter 234, the electronics 340 may take the form of or be similar in form to the controller 150 and/or the electronics 240, the electronics 350 may take the form or be similar in form to the controller 150 and/or the electronics 250, and the sensor 360 may take the form or be similar in form to the bio-analyte sensor 162 and/or the sensor 260.

The antenna 370 is configured for communications and/or harvesting energy, like the antenna 270 is configured for communications and/or harvesting energy. The antenna 370 includes a plurality of conductive loops 372 spaced apart from each other between the outer diameter 332 and the inner diameter 334. In the illustrated example, the plurality of conductive loops 372 includes three conductive loops 372A, 372B, and 372C. However, in other examples, a plurality of conductive loops may include more than three conductive loops, such as five conductive loops, nine conductive loops, etc. When the structure 330 is embedded in the transparent polymer 320, the conductive loops 372A, 372B, and 372C may move relative to each other.

The conductive loops 372A, 372B, and 372C can have an arrangement similar to an arrangement of the conductive loops 272A, 272B, and 272C. As shown in FIGS. 3*a* and 3*b*, the conductive loops 372A, 372B, and 272C are connected in parallel. With this arrangement, each of the conductive loops in the plurality of conductive loops 372 is electrically connected to the electronics 340, the electronics 350, and the sensor 360 via a first connection 374 and a second connection 376. And the electronics 340, the electronics 350, and the sensor 360 are electrically connected via the first connection 374 and the second connection 376. The first connection 374 and the second connection 376 may take the form of or be similar in form to the first connection 274 and the second connection 276 and/or the interconnects 151 and 157. Moreover, as shown in FIGS. 3*a* and 3*b*, the conductive loops 372A, 372B, and 372C are substantially concentric. And as shown in FIGS. 3*a* and 3*b*, the conductive loops 372A, 372B, and 372C are spaced apart from each other between the outer diameter 332 and the inner diameter 334.

The conductive loops 372A, 372B, and 372C may have a width that is the same or similar to a width of the conductive loops 272A, 272B, and 272C. Moreover, each of the conductive loops in the plurality of conductive loops 372 can comprise a respective metal layer disposed between respective polymer layers, like the conductive loops in the plurality of conductive loops 272 comprise a respective metal layer disposed between respective polymer layers. And the plurality of conductive loops 372 can be formed like the plurality of conductive loops 272 is formed.

In the illustrated example, the metal and polymer layers in each conductive loop in the plurality of conductive loops 372 are spaced apart from the metal and polymer layers in each adjacent conductive loop in the in the plurality of conductive loops 372. In some embodiments, the transparent polymer 320 can extend between adjacent conductive loops (e.g., the conductive loop 372A and the conductive loop 372B and/or the conductive loop 372B and the conductive loop 372C) in the plurality of conductive loops 372.

Moreover, in the illustrated example, the metal and polymer layers of conductive loop 372B are spaced apart from the metal and polymer layers of adjacent conductive loop 372A by a first distance 394, and the metal and polymer layers of conductive loop 372B are spaced apart from the metal and polymer layers of adjacent conductive loop 372C by a second distance 396. In an example, the first distance 394 and the second distance 396 can be between 100 to 200 micrometers. Other distances are possible as well.

The first distance 394 could be a different value than the second distance 396. In some embodiments, the first distance 394 can be greater (or less) than the second distance 396. And the first distance 394 and/or the second distance 396 could vary. In some embodiments, the first distance 394 can vary based on a rotational orientation of the conductive loop 372B relative to the conductive loop 372A and/or the conductive loop 372C. Moreover, in some embodiments, the second distance 396 can vary based on a rotational orientation of the conductive loop 372B relative to the conductive loop 372C and/or the conductive loop 372A.

FIG. 3c is a side cross-section view of the eye-mountable 310 while mounted to a corneal surface 384 of an eye 380, according to an example embodiment. FIG. 3d is a close-in side cross-section view enhanced to show tear film layers 390, 392 surrounding exposed surfaces 324, 326 of the eye-mountable device 310, according to an example embodiment. It is noted that relative dimensions in FIGS. 3c and 3d are not necessarily to scale, but have been rendered for purposes of explanation only in describing the arrangement of the eye-mountable electronic device 310. For example, the total thickness of the eye-mountable device 310 can be about 200 micrometers, while the thickness of the tear film layers 390, 392 can each be about 10 micrometers, although this ratio may not be reflected in the drawings. Some aspects are exaggerated to allow for illustration and facilitate explanation.

The eye 380 includes a cornea 382 that is covered by bringing the upper eyelid 386 and lower eyelid 388 together over the top of the eye 380. Incident light is received by the eye 380 through the cornea 382, where light is optically directed to light-sensing elements of the eye 380 (e.g., rods and cones, etc.) to stimulate visual perception. The motion of the eyelids 386, 388 distributes a tear film across the exposed corneal surface 384 of the eye 380. The tear film is an aqueous solution secreted by the lacrimal gland to protect and lubricate the eye 380. When the eye-mountable device 310 is mounted in the eye 380, the tear film coats both the anterior and posterior sides 324, 326 with an inner layer 390 (along the posterior side 326) and an outer layer 392 (along the anterior side 324). The tear film layers 390, 392 can be about 10 micrometers in thickness and together account for about 10 microliters.

The tear film layers 390, 392 are distributed across the corneal surface 384 and/or the posterior side 324 by motion of the eyelids 386, 388. For example, the eyelids 386, 388 raise and lower, respectively, to spread a small volume of tear film across the corneal surface 384 and/or the anterior side 324 of the eye-mountable device 310. The tear film layer 390 on the corneal surface 384 also facilitates mounting the eye-mountable device 310 by capillary forces between the anterior side 326 and the corneal surface 384. In some embodiments, the eye-mountable device 310 can also be held over the eye in part by vacuum forces against the corneal surface 384 due to the concave curvature of the eye-facing anterior side 326.

In some embodiments, a polymer layer defining the anterior side 326 may be greater than 50 micrometers thick, whereas a polymer layer defining the posterior side 324 may be less than 150 micrometers. Thus, when the sensor 360 is mounted on an outward-facing surface 335 (as shown in FIG. 3d) the sensor 360 may be at least 50 micrometers away from the anterior side 324 and may be a greater distance away from the posterior side 326. However, in other examples, the sensor 360 may be mounted on an inward-facing surface 333 of the structure 330 such that the sensor 360 is facing the posterior side 326. The sensor 360 could also be positioned closer to the anterior side 324 than the posterior side 326. With this arrangement, the sensor 360 can receive analyte concentrations in the tear film 392 via a channel 373. In some examples, analyte concentrations in the tear film 390 and/or 392 may diffuse through the transparent polymer 320 to the sensor 360. As a result, the eye-mountable device 310 might not include the channel 373.

While the body-mountable device has been described as comprising the eye-mountable device 110 and/or the eye-mountable device 310, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 310. For instance, the tooth-mountable device could include a polymeric material or a transparent polymer that is the same or similar to any of the polymeric materials or transparent polymers described herein and a substrate or a structure that is the same or similar to any of the substrates or structures described herein. With such an arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 110 and/or the eye-mountable device 310. For instance, the skin-mountable device could include a polymeric material or a transparent polymer that is the same or similar to any of the polymeric materials or transparent polymers described herein and a substrate or a structure that is the same or similar to any of the substrates or structures described herein. With such an arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 4:
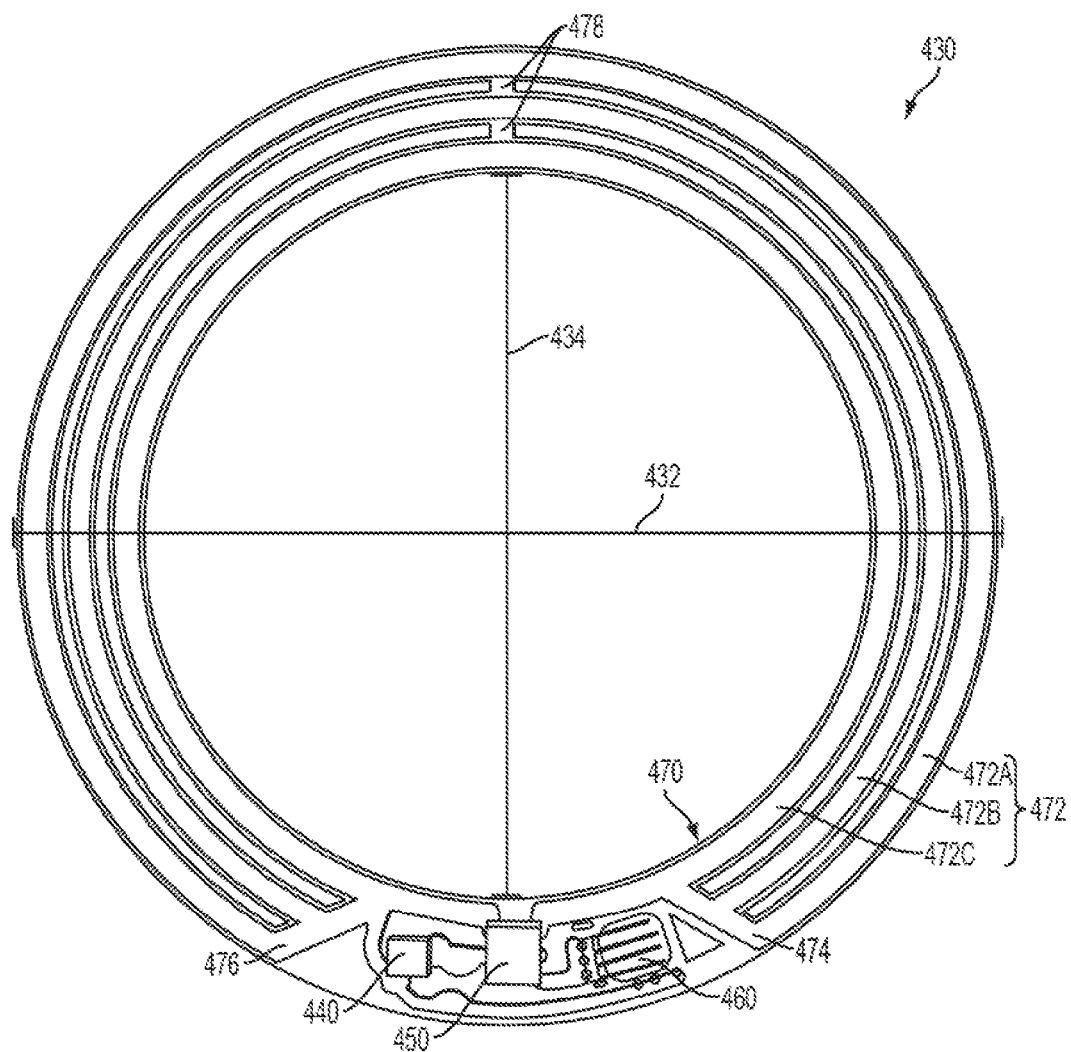
FIG. 4 is a top view of another structure, according to an example embodiment.

FIG. 4 is a top view of a structure 430, according to an example embodiment. In particular, the structure 430 includes a spacer 478 configured to maintain substantially uniform spacings between adjacent conductive loops in a plurality of conductive loops 472. The term "substantially uniform," as used in this disclosure, refers to exactly uniform and/or one or more deviations from exactly uniform that do not significantly impact embedding an structure in a body-mountable device as described herein.

More specifically, the structure 430 has an outer diameter 432 and an inner diameter 434 and includes electronics 440, electronics 450, a sensor 460, and an antenna 470 disposed thereon. The outer diameter 432 may take the form of or be similar in form to the outer diameter 232 and/or the outer diameter 332; the inner diameter 434 may take the form of or be similar in form to the inner diameter 234 and/or the inner diameter 334; the electronics 440 may take the form of or be similar in form to the controller 150, the electronics 240, and/or the electronics 340, the electronics 450 may take the form or be similar in form to the controller 150, the electronics 250, and/or the electronics 350; and the sensor 460 may take the form or be similar in form to the bio-analyte sensor 162, the sensor 260, and/or the sensor 360.

The antenna 470 is configured for communications and/or harvesting energy, like the antenna 270 and the antenna 370 are configured for communications and/or harvesting energy. As noted, the antenna 470 includes the plurality of conductive loops 472. The plurality of conductive loops 472 is spaced apart from each other between the outer diameter 432 and the inner diameter 434. In the illustrated example, the plurality of conductive loops 472 includes three conductive loops 472A, 472B, and 472C. However, in other examples, a plurality of conductive loops may include more than three conductive loops, such as five conductive loops, nine conductive loops, etc.

The conductive loops 472A, 472B, and 472C can have an arrangement similar to an arrangement of the conductive loops 272A, 272B, and 272C and/or the conductive loops 372A, 372B, and 372C. As shown in FIG. 4, the conductive loops 472A, 472B, and 472C are connected in parallel. With this arrangement, each of the conductive loops in the plurality of conductive loops 472 is electrically connected to the electronics 440, the electronics 450, and the sensor 460 via a first connection 474 and a second connection 476. And the electronics 440, the electronics 450, and the sensor 460 are electrically connected via the first connection 474 and the second connection 476. The first connection 474 and the second connection 476 may take the form of or be similar in form to the interconnects 151 and 157, the first connection 274 and the second connection 276, and/or the first connection 374 and the second connection 376.

Moreover, as shown in FIG. 4, the conductive loops 472A, 472B, and 472C are substantially concentric. And as shown in FIG. 4, the conductive loops 472A, 472B, and 472C are spaced apart from each other between the outer diameter 432 and the inner diameter 434. In an example, the conductive loops 472A, 472B, and 472C can be spaced apart from adjacent conductive loops by a distance between 100 to 200 micrometers. Other distances are possible as well.

The conductive loops 472A, 472B, and 472C may have a width that is the same or similar to a width of the conductive loops 272A, 272B, and 272C and/or the conductive loops 372A, 372B, and 372C. Moreover, each of the conductive loops in the plurality of conductive loops 472 can comprise a respective metal layer disposed between respective polymer layers, like the conductive loops in the plurality of conductive loops 272 comprise a respective metal layer disposed between respective polymer layers. And the plurality of conductive loops 472 can be formed like the plurality of conductive loops 272 and/or the plurality of conductive loops 372 is formed.

The structure 430 may be embedded in a transparent polymer, such as the transparent polymer 320. For instance, when the structure 430 is embedded in the transparent polymer, when each of the conductive loops in the plurality of conductive loops 472 comprise a respective metal layer disposed between respective polymer layers, the metal and polymer layers in each conductive loop in the plurality of conductive loops 472 can be spaced apart from the metal and polymer layers in each adjacent conductive loop in the plurality of conductive loops 472. And the transparent polymer can extend between adjacent conductive loops in the plurality of conductive loops 472.

As noted, the structure 430 includes the spacer 478. When the structure 430 is embedded in the transparent polymer the conductive loops 472A, 472B, and 472C may not move relative to each other based on the spacer 478.

As shown in FIG. 4, the spacer 478 is connected to the conductive loops 472A, 472B, and 472C and is located on the structure 430 substantially opposite of the sensor 260. Other locations of the spacer 478 on the structure 430 are possible as well. For instance, the spacer 478 could be located on the structure 430 at a predetermined rotational orientation, such as 30 degrees, 45 degrees, 60 degrees, 90 degrees, etc. The term "substantially opposite," as used in this disclosure, refers to exactly opposite (e.g., a rotational orientation of 180 degrees) or one or more deviations from exactly opposite that do not significantly impact embedding a structure in a body-mountable device as described herein.

The spacer 478 could take various different forms in various different embodiments. For example, in some embodiments, the spacer 478 can have a width between 50 and 300 micrometers. Other widths of the spacer 478 are possible as well. Moreover, in some embodiments, the spacer 478 can comprise a metal, such as gold, platinum, palladium, titanium, aluminum, copper, and/or silver. In some examples, the spacer 478 can comprise the same metal as the respective metal layers of the conductive loops 472A, 472B, and 472C. However, in other examples, the spacer 478 can comprise a different metal than the respective metal layers of the conductive loops 472A, 472B, and 472C. In an example, the spacer 478 can be formed by a process that includes electroplating.

Furthermore, in some embodiments, the spacer 478 can comprise a polymeric material, such as PET or paralyene. In some examples, the spacer 478 can comprise the same polymeric material as the respective polymer layers of the conductive loops 472A, 472B, and 472C. However, in other examples, the spacer 478 can comprise a different polymeric material than the respective polymer layers of the conductive loops 472A, 472B, and 472C. In an example, the spacer 478 can be formed by a process that includes chemical vapor deposition.

And in some embodiments, the spacer 478 can comprise a metal layer disposed between polymer layers, like the respective metal layers disposed between the respective polymer layers of the conductive loops 472A, 472B, and 472C.

In an example, the spacer 478 is formed by a process that includes etching a portion of a metal and/or a polymeric material with an inductively coupled plasma, such as an oxygen plasma.

In the illustrated example, the structure 430 includes one spacer, the spacer 478. However, in other examples, a structure may include more than one spacer, such as two spacers, three spacers, four spacers, etc. For instance, a structure could include one or more spacers configured to maintain substantially uniform spacings between adjacent conductive loops in a plurality of conductive loops. And each spacer in the one or more spacers could be located on the structure in a predetermined rotational orientation, such as 30 degrees, 45 degrees, 60 degrees, 90 degrees, etc. Each of the spacers in the one or more spacers could take the form or be similar in form to the spacer 478.

Figure 5:
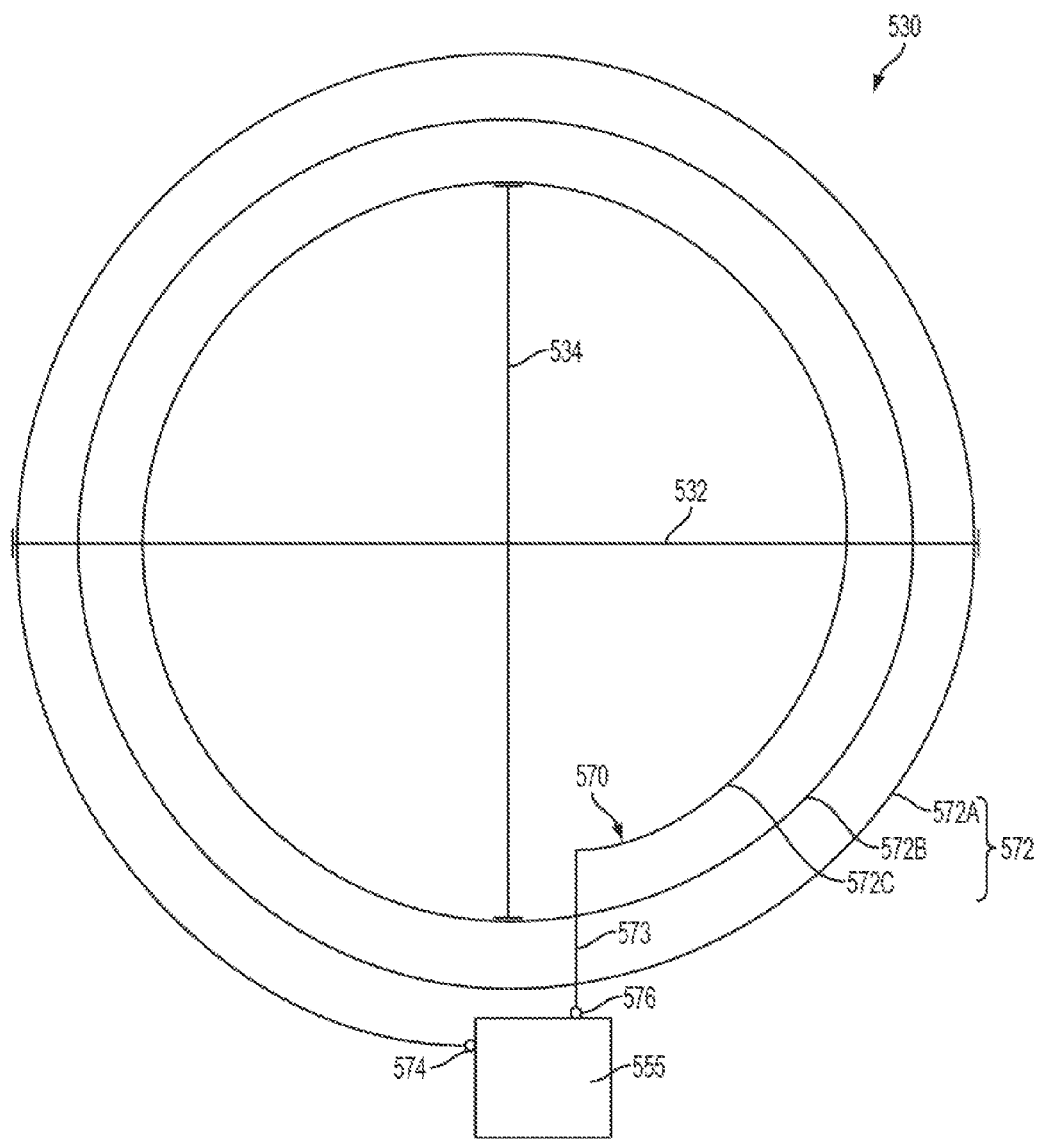
FIG. 5 is a top view of yet another structure, according to an example embodiment.

FIG. 5 is a top view of a structure 530, according to an example embodiment. In particular, the structure 530 includes an antenna 570 that includes a plurality of conductive loops 572 that includes three conductive loops 572A, 572B, and 572C. As shown in FIG. 5, the conductive loops 572A, 572B, and 572C are connected in series.

More specifically, the structure 530 has an outer diameter 532, and an inner diameter 534. The outer diameter 532 may take the form of or be similar in form to the outer diameter 232, the outer diameter 332, and/or the outer diameter 432; and the inner diameter 434 may take the form of or be similar in form to the inner diameter 234, the inner diameter 334, and or the inner diameter 434.

As noted, the structure 530 includes the antenna 570. The antenna 570 is configured for communications and/or harvesting energy, like the antenna 270, the antenna 370, and the antenna 470 are configured for communications and/or harvesting energy. The antenna 570 includes the plurality of conductive loops 572 spaced apart from each other between the outer diameter 532 and the inner diameter 534. In the illustrated example, the plurality of conductive loops 572 includes the conductive loops 572A, 572B, and 572C. However, in other examples, a plurality of conductive loops may include more than three conductive loops, such as five conductive loops, nine conductive loops, etc.

As noted, the conductive loops 572A, 572B, and 572C are connected in series. With this arrangement, the conductive loop 572A is electrically connected to an electrical component 555 via a first connection 574 and the conductive loop 572C is electrically connected to the electrical component 555 via a second connection 576. The electrical component 555 could include electronics (e.g., the controller 150, the electronics 240, the electronics 250, the electronics 340, the electronics 350, the electronics 440, and/or the electronics 450) and/or a sensor (e.g., the analyte bio-sensor 162, the sensor 260, the sensor 360, and/or the sensor 460). When the electrical component 555 includes more than one component, the more than one component could be arranged in series.

As shown in FIG. 5, the conductive loop 572C is connected to the second connection via a bridge 573. The bridge 573 may insulate the conductive loop 572C from the conductive loop 572B and/or the conductive loop 572A. In some embodiments, the bridge 573 can comprise a polymeric material, such as PET or paralyene. And in some examples, the bridge 573 can comprise the same polymeric material as the spacer 478 and/or the respective polymer layers of the conductive loops 272A, 272B, and 272C, the conductive loops 372A, 372B, and 372C, and/or the conductive loops 472A, 472B, and 472C. However, in other examples, the bridge 573 can comprise a different polymeric material than the spacer 478 and/or the respective polymer layers. The bridge 573 may be other materials as well, such as silicon. Moreover, in some embodiments, the bridge 573 may include an integrated circuit. And in at least one such embodiment, the conductive loop 572A, the conductive loop 572B, and the conductive loop 572C may cross at the bridge 573.

In the illustrated example, the plurality of conductive loops 572 is a continuous material arranged in multiple windings, shown as the conductive loops 572A, 572B, and 572C. However, in other examples, a plurality of conductive loops may not be a continuous material.

As shown in FIG. 5, the conductive loops 572A, 572B, and 572C are substantially concentric. And as shown in FIG. 5, the conductive loops 572A, 572B, and 572C are spaced apart from each other between the outer diameter 532 and the inner diameter 534. In an example, the conductive loops 572A, 572B, and 572C are spaced apart from adjacent conductive loops by a distance between 100 to 200 micrometers. Other distances are possible as well.

The conductive loops 572A, 572B, and 572C may have a width that is the same or similar to a width of the conductive loops 272A, 272B, and 272C; the conductive loops 372A, 372B, and 372C; and/or the conductive loops 472A, 472B, and 472C. Moreover, each of the conductive loops in the plurality of conductive loops 572 can comprise a respective metal layer disposed between respective polymer layers, like the conductive loops in the plurality of conductive loops 272 comprise a respective metal layer disposed between respective polymer layers. In an example, the conductive loops 572A, 572B, and 572C can be formed by a process that includes electroplating, chemical vapor deposition, and etching, using an inductively coupled plasma, such as oxygen plasma.

The structure 530 may be embedded in a transparent polymer, like the structure 330 is embedded in the transparent polymer 320. When the structure 530 is embedded in the transparent polymer, the conductive loops 572A, 572B, and 572C may move relative to each other. In an example, movement of the conductive loops 572A, 572B, and 572C may be the same as movement of the conductive loops 372A, 372B, and 372C. However, in other examples, movement of the conductive loops 572A, 572B, and 572C may be greater (or less) than movement of the conductive loops 372A, 372B, and 372C.

For instance, when the structure 530 is embedded in the transparent polymer and each of the conductive loops in the plurality of conductive loops 572 comprise a respective metal layer disposed between respective polymer layers, the metal and polymer layers in each conductive loop in the plurality of conductive loops 572 can be spaced apart from the metal and polymer layers in each adjacent conductive loop in the plurality of conductive loops 572. And the transparent polymer can extend between adjacent conductive loops in the plurality of conductive loops 572.

Moreover, the metal and polymer layers of conductive loop 572B can be spaced apart from the metal and polymer layers of adjacent conductive loop 572A by a first distance, and the conductive loop 572B may be spaced apart from the adjacent conductive loop 572C by a second distance. The first and second distances can be between 100 to 200 micrometers. Other distances are possible as well.

The first distance could be a different value than the second distance. For instance, the first distance can be greater (or less) than the second distance. And the first distance and/or the second distance could vary. As one example, the first distance can vary based on a rotational orientation of the conductive loop 572B and/or the conductive loop 572C relative to the conductive loop 572A. Moreover, in some embodiments, the second distance can vary based on a rotational orientation of the conductive loop 572C and/or the conductive loop 572A relative to the conductive loop 572B.

III. Example Methods

Figure 6:
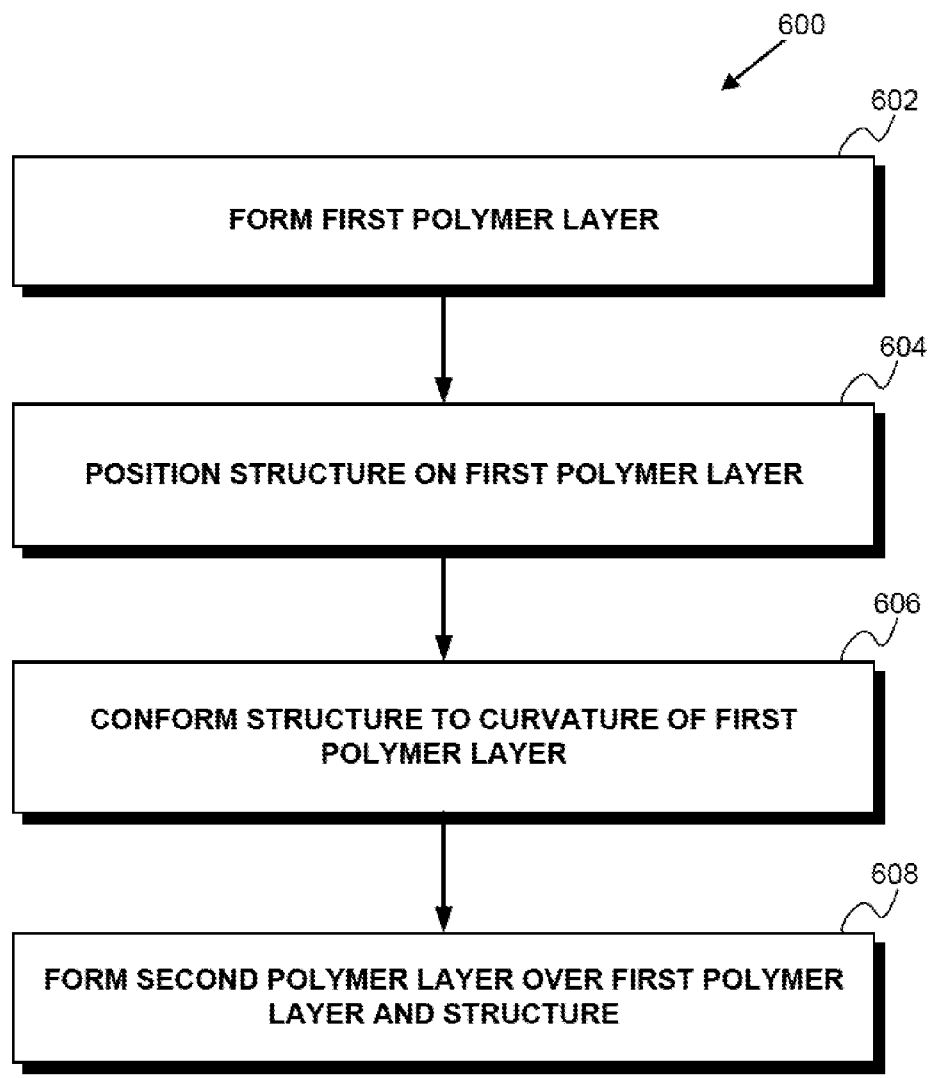
FIG. 6 is a flow chart illustrating a method, according to an example embodiment.

FIG. 6 is a flow chart illustrating a method, according to an example embodiment. More specifically, the method 600 involves forming a first polymer layer, as shown by block 602. The method 600 may then involve positioning a structure on the first polymer layer, as shown by block 604. Further, the method 600 may then involve conforming the structure positioned on the first polymer layer to a curvature of the first polymer layer, as shown by block 606. The method 600 may then involve forming a second polymer layer over the first polymer layer and the structure, as shown by block 608.

For purposes of illustration, the method 600 is described below as being carried out by a fabrication device that utilizes cast or compression molding. It should be understood, however, that method 600 may be carried out by a fabrication device that utilizes other methods for forming the polymer layers.

Moreover, for purposes of illustration, the method 600 is described below in a scenario where a body-mountable device comprises an eye-mountable device. It should be understood, however, that the method 600 may involve scenarios where the body-mountable device comprises other mountable devices that are mounted on or in other portions of the human body. For example, the method 600 may involve scenarios where the body-mountable device comprises a tooth-mountable device and/or a skin-mountable device as described herein.

A. Forming a First Polymer Layer

Figure 7A:
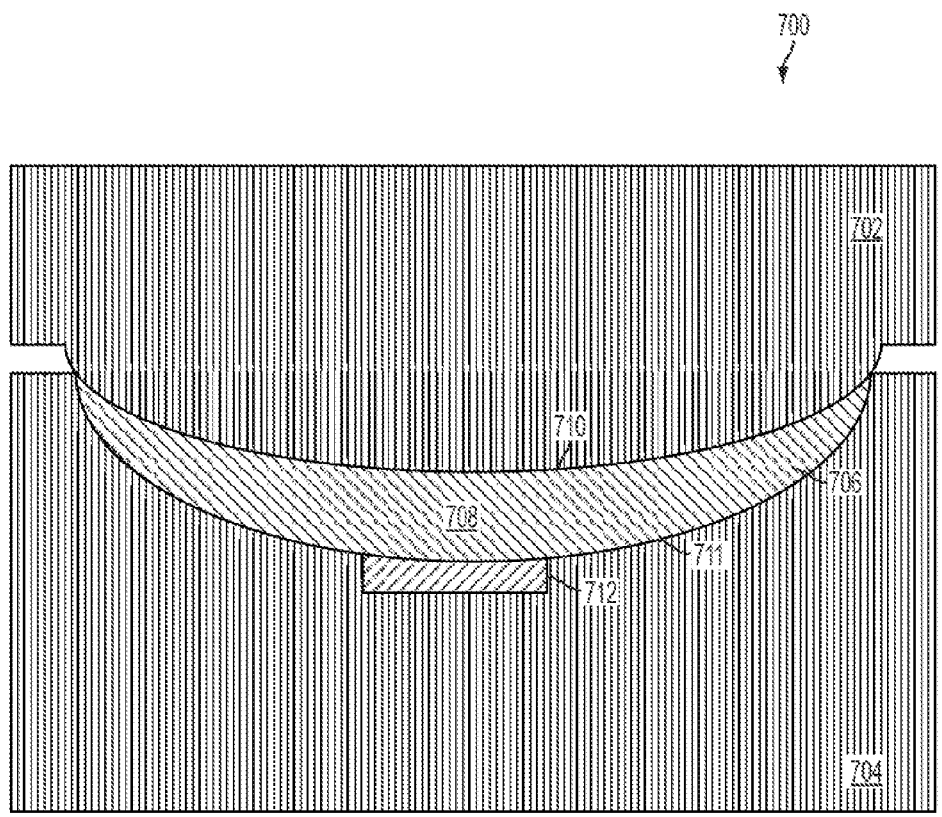
FIG. 7a is an illustration of formation of a first polymer layer, according to an example embodiment.

As mentioned above, at block 602, the fabrication device may be used to form a first polymer layer. The fabrication device may include molding pieces, such as molding pieces that are suitable for cast molding. FIG. 7a illustrates a fabrication device 700 that includes example molding pieces that may be used to form the first polymer layer. In particular, FIG. 7a illustrates a fabrication device 700 including a first molding piece 702 and a second molding piece 704. The first molding piece 702 and the second molding piece 704 may define a first cavity. The second molding piece 704 may be filled with a polymer material 706, and the polymer material 706 may be compressed into a first polymer layer 708 by the first molding piece 702.

After the polymer material 706 is compressed into the first polymer layer 708, the fabrication device 700 may cure the first polymer layer 708. Curing involves the hardening of a polymer material by cross-linking of polymer chains, and curing may be, for example, brought about by chemical additives, ultraviolet radiation, electron beam, and/or heat. In an example, the polymer material 706 can be a light-curable polymer material, and the fabrication device 700 may be configured to cure the light-curable polymer material using light, such as ultraviolet light or visible light.

In an example, the first polymer layer 708 may be cured to a partially-cured state. In an example, this may involve curing the material to a partially-cured state that is approximately 50-75% of a fully cured state. Other partially-cured states are possible as well. Beneficially, by partially curing the first polymer layer to a partially-cured state, the first polymer layer 708 may have a tackiness that facilitates adhesion thereto. With this arrangement, the tackiness may ensure that a structure conformed to a curvature of the first polymer layer 708 remains securely fixed in a given location during subsequent formation steps.

The tackiness exhibited by the partially-cured first polymer layer 708 may be different for different polymers. Accordingly, the fabrication device 700 may be configured to cure different polymer materials differently than other polymer materials (e.g., a first polymer material may be cured more than a second polymer material). Further, in addition to light curing, other methods of curing are possible as well, such as chemical additives and/or heat. Yet still further, in other example embodiments, the first polymer layer may be completely cured. Alternatively, the fabrication device 700 may bypass the curing process at this stage.

The first molding piece 702 and the second molding piece 704 may be configured to achieve a given desired thickness of the first polymer layer 708. For instance, in an example, the first polymer layer 708 can have a thickness of less than 150 micrometers. In an example embodiment, the first molding piece 702 and the second molding piece 704 can be designed so as to allow for a layer having less than a 150 micrometer thickness between the two cavities. As such, when the first molding piece 702 and the second molding piece 704 are pressed together during the formation of the first polymer layer 708, the resulting polymer layer 708 will have a thickness of less than 150 micrometers.

In an example, the thickness of the first polymer layer 708 can be selected based on a particular analyte or analytes an eye-mountable device is configured to detect. For example, an optimal thickness for a first analyte may be 10 micrometers, while an optimal thickness for a second analyte may be 25 micrometers. Other examples are possible as well.

In an example, the polymer material 706 can be any material that can form an eye-compatible polymer layer. For example, the polymer material 706 may be a formulation containing polymerizable monomers, such as hydrogels, silicone hydrogels, silicone elastomers, and rigid gas permeable materials. Further, the polymer material 706 may form a transparent or substantially transparent polymer layer. As such, the use of the polymer material 706 may result in an eye-mountable device through which the wearer can see when mounted on the wearer's eye. In an example, the polymer material 706 can be a hydrogel material, such as silicone hydrogel. As known in the art, hydrogel materials are commonly used in contact-lens technology and are well-suited for eye-mountable devices. Other materials are possible as well.

In an example, the first molding piece 702 and/or the second molding piece 704 can be configured so as to allow sufficient pinch off to provide for suitable edges for an eye-mountable device.

The first polymer layer 708 defines a posterior side 710 of an eye-mountable device. That is, the first polymer layer 708 defines an outer edge of the eye-mountable device. When mounted on an eye of a user, the posterior side 710 of the eye-mountable device defined by the first polymer layer 708 corresponds to a side of the device touching the eye of the user. The first molding piece 702 may be shaped so as to define a shape of the posterior side 710. For example, a curvature of the posterior side 710 may be defined by the first molding piece 702. The second molding piece 704 may be shaped so as to define a shape of a positioning surface 711 of the first polymer layer. For example, the second molding piece 704 may define a curvature of a positioning surface 711 of the first polymer layer 708. In an example, a structure can be conformed to the curvature of the positioning surface 711 of the first polymer layer 708.

The first polymer layer 708 can further comprise an alignment feature 712. In an example, the alignment feature 712 can comprise an asymmetric peg. The asymmetric peg can be a variety of shapes. For instance, the asymmetric peg can have a star-shaped or cross-shaped cross section. Other shapes of the asymmetric peg are possible as well.

As mentioned above, although FIG. 7a illustrates forming the first polymer layer 708 through cast molding, other methods for forming first polymer layer 708 are possible as well. For example, the first polymer layer 708 may be formed via injection molding. In injection molding, rather than polymer material being compressed between molding pieces, molding material may be heated and injected or otherwise forced into a molding piece or pieces. The injected molding material may then cool and harden to the configuration of the molding piece or pieces.

As another example, the first polymer layer 708 may be formed via spin casting. Through spin-casting techniques, the fabrication device may form a first polymer layer of a precise thickness. In an example, a spin-casting mold may be spun along its central access at a set speed, and the polymer may be introduced to the mold as the mold is spinning in order to form a first polymer layer. The final thickness of the first polymer layer may be influenced by various factors, including but not limited to the spin-casting mold, the amount of polymer introduced to the spin-casting mold, properties of the polymer such as viscosity, and/or the speed at which the spin-casting mold is rotated. These factors may be varied in order to result in a first polymer layer of a well-defined thickness.

B. Positioning a Structure on the First Polymer Layer

Figure 7B:
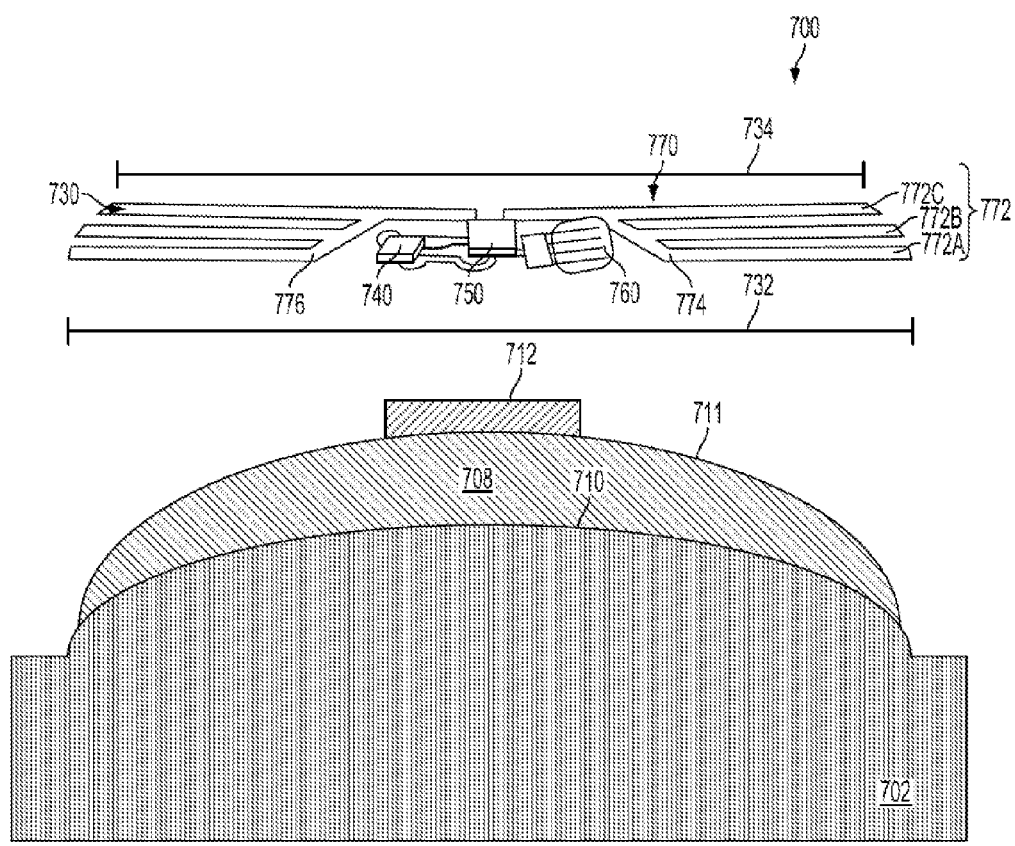
FIG. 7b is an illustration of positioning a structure on a first polymer layer, according to an example embodiment.
Figure 7C:
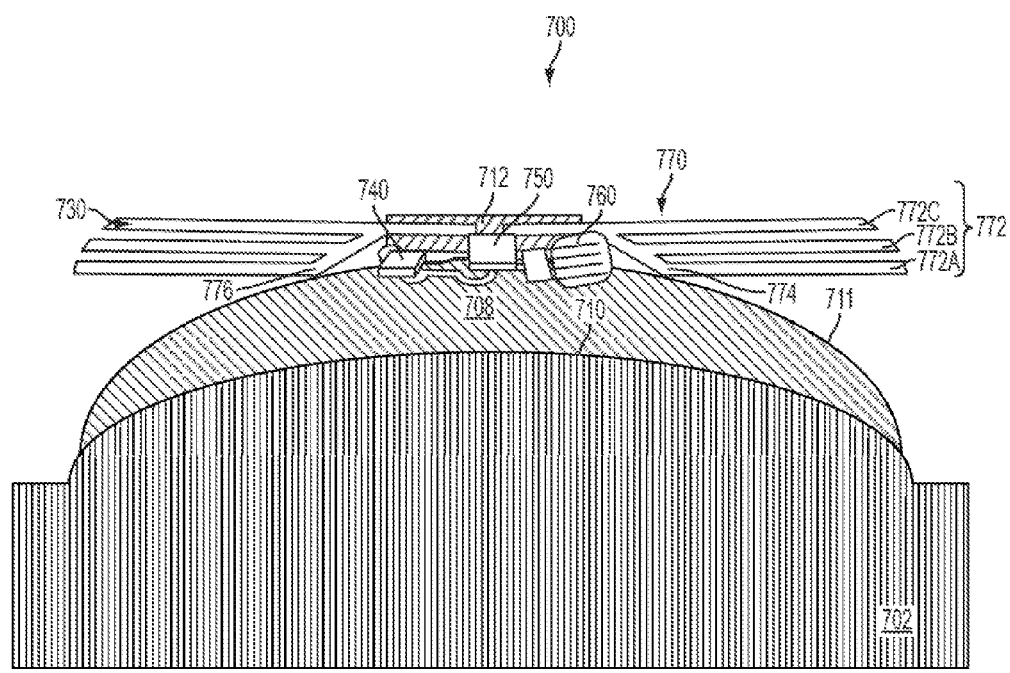
FIG. 7c is an illustration of a structure positioned on a first polymer layer, according to an example embodiment.

As mentioned above, at block 604, a structure may be positioned on the first polymer layer. FIGS. 7b and 7c illustrate an example in which a structure 730 is positioned on the first polymer layer 708.

The structure 730 has an outer diameter 732 and an inner diameter 734 and includes electronics 740, electronics 750, a sensor 760, and an antenna 770 disposed thereon. The structure 730 may take the form of or be similar in form to the substrate 130, the structure 230, the structure 330, the structure 430 and/or the structure 530. In some embodiments, the structure 730 can further include one or more spacers, such as the spacer 478.

The outer diameter 732 may take the form of or be similar in form to the outer diameter 232, the outer diameter 332, the outer diameter 432, and/or the outer diameter 532; the inner diameter 734 may take the form of or be similar in form to the inner diameter 234, the inner diameter 334, and or the inner diameter 434 and/or the outer diameter 534; the electronics 740 may take the form or be similar in form to the controller 150, the electronics 240, the electronics 340, the electronics 440 and/or the electronics 555; the electronics 750 may take the form of or be similar in form to the controller 150, the electronics 250, the electronics 350, the electronics 450, and/or the electronics 555; and the sensor 760 may take the form of or be similar in form to the bio-analyte sensor 162, the sensor 260, the sensor 360, the sensor 460.

As noted, the structure 730 includes the antenna 770. The antenna 770 is configured for communications and/or harvesting energy, like the antenna 270, the antenna 370, the antenna 470, and the antenna 570 are configured for communications and/or harvesting energy. The antenna 770 includes a plurality of conductive loops spaced 772 apart from each other between the outer diameter 732 and the inner diameter 734. In the illustrated example, the plurality of conductive loops 772 includes three conductive loops 772A, 772B, and 772C. However, in other examples, a plurality of conductive loops may include more than three conductive loops, such as five conductive loops, nine conductive loops, etc.

As shown in FIG. 7b, the conductive loops 772A, 772B, and 772C are substantially concentric. And as shown in FIG. 7b, the conductive loops 772A, 772B, and 772C are spaced apart from each other between the outer diameter 732 and the inner diameter 734. In an example, the conductive loops 772A, 772B, and 772C are spaced apart from adjacent conductive loops by a distance between 100 to 200 micrometers. Other distances are possible as well. In the illustrated example, the conductive loops 772A, 772B, and 772C are connected in parallel. However, in other examples, conductive loops can be connected in series, like the conductive loops 572A, 572B, and 572C are connected in series.

In order to position the structure 730, the fabrication device 700 may separate the first molding piece 702 from the second molding piece 704. When the fabrication device 700 separates the first molding piece 702 from the second molding piece 704, the first polymer layer 708 may stick to a side of the first molding piece 702. In an example, the first polymer layer 708 and/or the first molding piece 702 can be surface treated, such that the first polymer layer 708 sticks to the side of the first molding piece 702. Additionally or alternatively, the second molding piece 704 can be surface treated, such that the first polymer layer 708 sticks to the side of the first molding piece 702.

In an example, positioning the structure 730 on the first polymer layer 708 can include aligning the structure 730 with the alignment feature 712. In one example, the inner diameter 734 can be asymmetric and the alignment feature 712 includes an asymmetric peg such that the inner diameter 734 receives the alignment feature 712 in only a predetermined rotational orientation (relative alignment between the alignment feature 712 and the inner diameter 734 in FIG. 7c is not necessarily to scale). However, other ways of providing a predetermined rotational orientation of the structure 730 by alignment with the alignment feature 712 are also possible.

Alternatively, the fabrication device 700 can include a positioning apparatus (not shown), such as a robotic system, configured to position the structure 730 on the first polymer layer 708. For instance, the positioning apparatus may (i) pick up the structure 730 (e.g., via suction), (ii) position the structure 730 above the first polymer layer 708, and then (iii) lower the structure 730 toward the first polymer layer 708. With this arrangement, the positioning apparatus may position the structure 730 in a predetermined rotational orientation. When the structure 730 is positioned in a predetermined orientation, the positioning apparatus may then release the structure 730 (e.g., by releasing the suction). With this approach, the first polymer layer 708 might not include the alignment feature 712.

The positioning apparatus may further include a vision system configured to assist with positioning the structure 730 on the first polymer layer 708. Such a vision system may facilitate guiding the structure 730 to a precise location on the first polymer layer 708. In an example, the vision system can be appropriate for situations in which one or more production specifications for an eye-mountable device, such as the eye-mountable device 310, have requirements with very low tolerances related to the positioning of a sensor, such as the sensor 360, within the eye-mountable device 310.

In some situations, such as for large-scale production purposes, it may be desirable to not only place the structure 730 in a predetermined orientation, but it may also be desirable to repeatedly place and maintain the structure 730 at this precise location for a plurality of eye-mountable devices. Beneficially, fabrication of an eye-mountable device in accordance with an example embodiment allows for such repeatable and precise positioning.

FIG. 7c illustrates the structure 730 positioned on the first polymer layer 708. With this arrangement, the sensor 760 may be mounted at a particular angle along a circumference of the first polymer layer 708. As a result, the sensor 760 may be placed at a precise location in an XYZ plane on the first polymer layer 708. As one example, the sensor 760 may rest at a 6 o'clock position of the first polymer layer 708. As another example, the sensor 760 may rest at a 12 o'clock position of the first polymer layer 708.

Figure 7D:
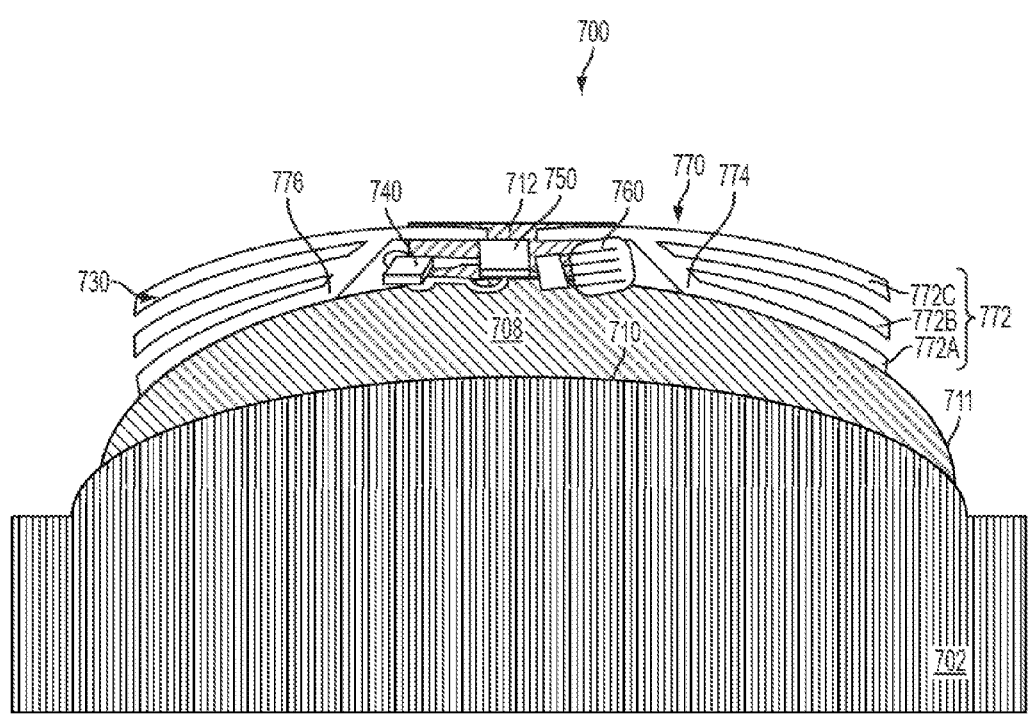
FIG. 7d is an illustration of conforming a structure positioned on a first polymer layer to a curvature of the first polymer layer, according to an example embodiment.

C. Conforming the Structure Positioned on the First Polymer Layer to a Curvature of the First Polymer Layer As mentioned above, at block 606, the structure positioned on the first polymer layer may be conformed to a curvature of the first polymer layer. FIG. 7d illustrates an example in which the structure 730 is conformed to the curvature of the positioning surface 711 of the first polymer layer 708.

In an example, conforming the structure 730 to the curvature of the positioning surface 711 of the first polymer layer can include bending the structure 730. In one example, the positioning apparatus may bend the structure 730, such that the structure 730 conforms to the curvature of the positioning surface 711 of the first polymer layer 708. The positioning apparatus may bend the structure 730 by applying a force and/or a torque to one or more portions of the structure 730. However, other ways of conforming the structure 730 to the curvature of the positioning surface 711 are possible as well.

Moreover, in an example, during conforming the conductive loops 772A, 772B, and 772C may move relative to each other. Beneficially, such movement can reduce buckling of the structure 730 when it is conformed to a curvature of the first polymer layer, such as the curvature of the positioning surface 711 of the first polymer layer 708. An amount and/or type of movement of the conductive loops 772A, 772B, and 772C may be based on a variety of parameters, such as a material, a width, a thickness, and/or a connection (e.g., parallel or series) of the conductive loops 772A, 772B, and 772C and/or a material, a thickness, and a curvature of the first polymer layer 708. Other parameters are possible as well. And in embodiments where the structure 730 further includes one or more spacers, such as the spacer 478, the conductive loops 772A, 772B, and 772C may not move relative to each other based on the one or more spacers.

During fabrication of an eye-mountable device, such as the eye-mountable device 310, it may be desirable for the structure 730 to remain in a fixed position during fabrication of the eye-mountable device. For instance, movement of the structure 730 during subsequent formation steps, such as formation of a second polymer layer, may result in improper placement of the structure 730 relative to the surrounding polymer layers. As one example, movement of the structure 730 during filling a mold piece with a polymeric material to form the second polymer layer and/or curing the second polymer layer can result in improper placement of the structure 730 relative to the surrounding polymer layers.

Therefore, in an example, an adhesive is applied to the structure 730 and/or the first polymer layer 708 before the structure 730 is positioned on the first polymer layer 708. The applied adhesive may facilitate adhesion of the structure 730 to the first polymer layer 708. For instance, a small amount of adhesive may be applied to a cured first polymer layer 708, and the structure 730 may be conformed to a curvature of the first polymer layer 708 and then the adhesive may be cured such that the structure 730 adheres to the first polymer layer 708. Additionally or alternatively, a small amount of adhesive may be applied to the structure 730, and the structure 730 may then be conformed to a curvature of the first polymer layer 708 (e.g., a cured first polymer layer) and then the adhesive may be cured such that the structure 730 adheres to the first polymer layer 708. With this arrangement, the structure 730 may remain adhered to the first polymer layer 708 in a secure location during subsequent formation steps. In some embodiments, a force and/or a torque can be applied to the structure 730 during curing of the adhesive.

As noted above, in an example, the first polymer layer 708 in a partially-cured state may have a tackiness that facilitates adhesion thereto. With this arrangement, the structure 730 may remain adhered to the first polymer layer 708 in a secure location during subsequent formation steps.

Figure 7E:
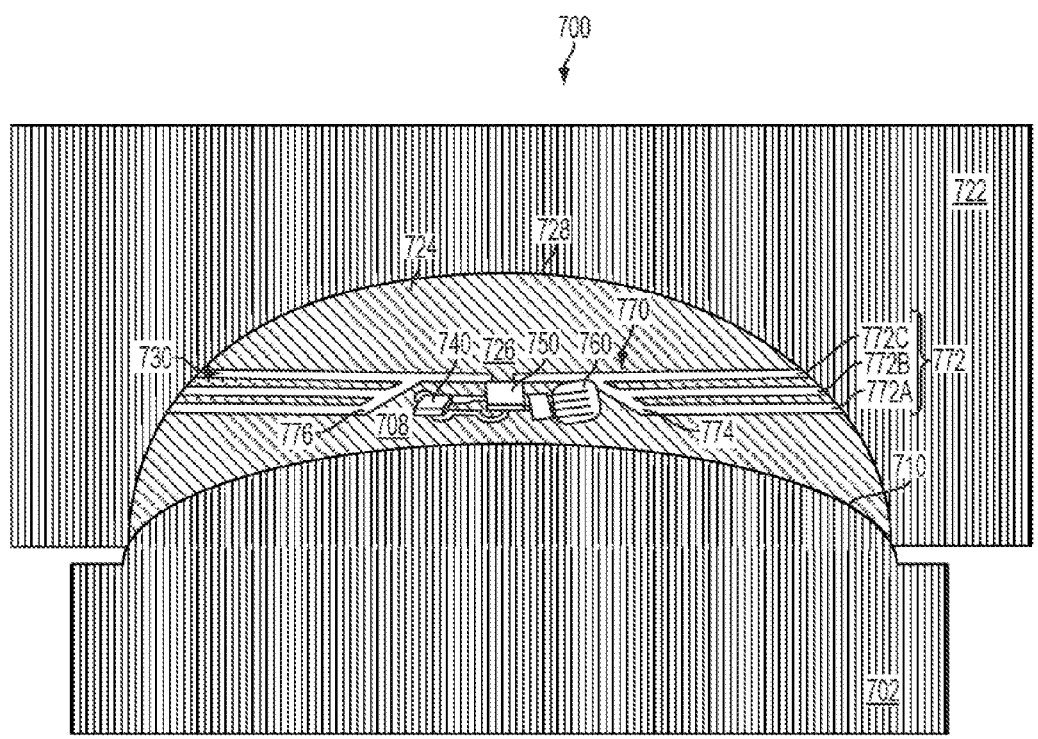
FIG. 7e is an illustration of formation of a second polymer layer, according to an example embodiment.

D. Forming a Second Polymer Layer Over the First Polymer Layer and the Structure As mentioned above, at block 608, the fabrication device may form a second polymer layer over the first polymer layer and the structure, such that the structure is fully enclosed by the first polymer layer and the second polymer layer. FIG. 7e illustrates the fabrication device 700 including example molding pieces that may be used to form the second polymer layer. In particular, FIG. 7e illustrates a third molding piece 722. The first molding piece 702 and the third molding piece 722 may define a second cavity.

The first molding piece 702, which already holds the first polymer layer 708 to which the structure 730 is mounted (as illustrated in FIG. 7d), may be filled with a polymer material 724. The polymer material 724 may be formed into a second polymer layer 726 by compression between the first molding piece 702 and the third molding piece 722. As a result, the second polymer layer 726 may mold over the structure 730, such that the structure 730 is fully enclosed by the first polymer layer 708 and the second polymer layer 726. In some embodiments, the second polymer layer can extend between adjacent conductive loops, such as the conductive loop 772A and the conductive loop 772B and/or the conductive loop 772B and the conductive loop 772C, in the plurality of conductive loops 772. With this arrangement, the second polymer layer 726 may bond to the first polymer layer 708 between the adjacent conductive loops in the plurality of conductive loops 772.

After the second polymer layer 726 is formed, the fabrication device 700 may cure the second polymer layer 726. In an example, the second polymer layer 726 can be cured like the first polymer layer 708. However, in other examples, the second polymer layer 726 may be cured by different techniques than the first polymer layer 708. The second polymer layer 726 can be cured by any of the techniques mentioned herein. In an example, the fabrication device 700 may cure the first polymer layer 708 at this stage.

After the second polymer layer 726 is cured, there may not be a visible boundary line separating the first polymer layer 708 from the second polymer layer 726. As noted, FIG. 3a illustrates the eye-mountable device 310. In particular, FIG. 3a illustrates the eye-mountable device 300 includes the transparent polymer 320. The transparent polymer 320 can be arranged like the first polymer layer 708 and the second polymer layer 726.

Returning to FIG. 7e, the fabrication device 700 may further comprise one or more alignment pins (not shown), such as a plurality of dowel pins, for aligning the third molding piece 722 and the first molding piece 702. The one or more alignment pins can assist in forming the second polymer layer 726 by aligning the third molding piece 722 with the first molding piece 702.

The first molding piece 702 and the third molding piece 722 may be configured to achieve a given desired thickness of a layer formed between the two pieces. As one example, the first molding piece 702 and the third molding piece 722 may be designed so as to define a thickness of the second polymer layer 726. As another example, the first molding piece 702 and the third molding piece 722 may be designed so as to define a final thickness of an eye-mountable device, such as the eye-mountable device 310. In an example, the first molding piece 702 and the third molding piece 722 can be designed so as to allow for a layer having a given desired thickness between the two pieces (in addition to a thickness of the first polymer 708). As such, when the first molding piece 702 and the third molding piece 722 are pressed together during formation of a layer, the resulting layer will have the given desired thickness.

In an example, the second polymer layer 726 has a thickness of greater than 50 micrometers. However, in other examples, the second polymer layer 726 can have a thickness between 50 and 300 micrometers, such as 130 micrometers. It should be understood that since the second polymer layer 726 molds over the structure 730, the second polymer layer 726 may not have a uniform thickness. For instance, the thickness of the second polymer layer 726 above the sensor 760 may be less than the thickness of the second polymer layer 726 that is not touching the sensor 760.

In an example, the thickness of the second polymer layer 726 can be selected based on a particular analyte or analytes that the eye-mountable device, such as the eye-mountable device 310, is configured to detect. For example, an optimal thickness for a first analyte may be 10 micrometers, while an optimal thickness for a second analyte may be 25 micrometers. Other examples are possible as well.

In an example, the second polymer layer 726 can be composed of the same polymer material as the first polymer layer 708. However, in other examples, the second polymer layer 726 can be composed of a different polymer material than the first polymer layer 708. The second polymer layer 726 can be any one of the polymer materials mentioned herein. In an example, the structure 730 can be more rigid than the second polymer layer 726.

The second polymer layer 726 defines an anterior side 728 of an eye-mountable device. That is, the second polymer layer 726 defines an outer edge of the eye-mountable device. When mounted on an eye of a user, the anterior side 728 of the eye-mountable device defined by the second polymer layer 726 corresponds to the side of the device that is not touching the eye of the user. The third molding piece 722 may be shaped so as to define a shape of the anterior side 728. For example, a curvature of the anterior side 728 may be defined by the third molding piece 722.

E. Forming the First Polymer Layer and the Second Polymer Layer at the Same Time The example methods described above involve a method of fabricating an eye-mountable device that involves first forming a first polymer layer and subsequently forming a second polymer layer. In another example, the first polymer layer defining a posterior side of the eye-mountable device and the second polymer layer defining an anterior side of the eye-mountable device may be substantially formed around a structure, such as the structure 730, at the same time. The term "substantially formed," as used in this disclosure, refers to exactly formed and/or one or more deviations from exactly formed that do not significantly impact embedding a structure in a body-mountable device as described herein. Further, in such an example, positioning the structure on the first layer and conforming the structure positioned on the first layer to a curvature of the first layer would take place at the same time as the formation of the first polymer layer and the second polymer layer.

For instance, in accordance with an example embodiment, the fabrication device may be configured to position a structure within a molding cavity or cavities, and the fabrication device may then form the first polymer layer and the second polymer layer around the structure. In such an example, the fabrication device may be configured to inject mold into the molding cavity, and the injected mold may encapsulate the structure. In this example, the fabrication device may include a molding cavity or cavities that have at least one opening configured to allow the fabrication device to hold the structure in place as the first and second polymer layers are formed around the structure. The molding cavity or cavities may be filled with the polymer material, and this introduction of the polymer material may form the polymer layers around the structure.

F. Forming a Channel Through the Second Polymer Layer

In some embodiments, the example methods described above may further include forming a channel through a second polymer layer, such that a sensor (e.g., sensor 760), is configured to receive one or more analytes via the channel. In such an example, the channel may be formed by removing material from the second polymer layer. The material from the second polymer layer can be removed to form the channel in a variety of ways. For instance, the material from the second polymer layer can be removed to form the channel via a process that includes drilling, ablation, etching, etc.

In another example, a mask layer may be formed before forming the second polymer layer. Further, in such an example, after the second polymer layer is formed, the mask layer may be removed to form a channel. The mask layer can be removed to form the channel in a variety of ways. For instance, the mask layer can be removed to form the channel via a process that includes etching the mask layer and/or dissolving the mask layer in a fluid.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The invention claimed is:

1. A body-mountable device comprising:
   a transparent polymer, wherein the transparent polymer defines a posterior side and an anterior side of the body-mountable device; and
   a structure embedded in the transparent polymer, wherein the structure has an outer circumference defined by an outer diameter and an inner circumference defined by an inner diameter and includes a sensor configured to detect an analyte, electronics, and an antenna, wherein the antenna includes a plurality of conductive loops spaced apart from each other between the outer circumference and the inner circumference, wherein, with respect to a vertical axis between the anterior side of the body-mountable device and the posterior side of the body-mountable device, a particular conductive loop in the plurality of conductive loops is spaced vertically apart and horizontally apart from an adjacent conductive loop in the plurality of conductive loops,
   wherein each conductive loop in the plurality of conductive loops comprises a respective metal layer disposed between a first respective polymer layer and a second respective polymer layer, and wherein the respective metal layer, the first respective polymer layer, and the second respective polymer layer are each embedded in the transparent polymer,
   wherein the transparent polymer extends from the anterior side of the body-mountable device to the posterior side of the body-mountable device between adjacent conductive loops in the plurality of conductive loops, and
   wherein each conductive loop in the plurality of conductive loops is connected to a first interconnect and a second interconnect, wherein the electronics and sensor are disposed between the first and second interconnects, and wherein each conductive loop in the plurality of conductive loops is electrically connected to the electronics and sensor via the first and second interconnects.

2. The body-mountable device of claim 1, wherein the body-mountable device comprises an eye-mountable device.

3. The body-mountable device of claim 1, wherein the body-mountable device comprises a tooth-mountable device.

4. The body-mountable device of claim 1, wherein the body-mountable device comprises a skin-mountable device.

5. The body-mountable device of claim 1, wherein the conductive loops are substantially concentric.

6. The body-mountable device of claim 1, wherein the plurality of conductive loops comprises at least three conductive loops.

7. The body-mountable device of claim 1, wherein the metal and first and second polymer layers in each conductive loop are spaced apart from the metal and first and second polymer layers in each adjacent conductive loop in the plurality of conductive loops.

8. The body-mountable device of claim 7, wherein the metal and first and second polymer layers of a particular conductive loop in the plurality of conductive loops are spaced apart from the metal and first and second polymer layers of a first adjacent conductive loop in the plurality of conductive loops by a first distance, and wherein the metal and first and second polymer layers of the particular conductive loop are spaced apart from the metal and first and second polymer layers of a second adjacent conductive loop in the plurality of conductive loops by a second distance.

9. The body-mountable device of claim 8, wherein the first distance varies based on a rotational orientation of the particular conductive loop relative to the first adjacent conductive loop.

10. The body-mountable device of claim 8, wherein the second distance varies based on a rotational orientation of the particular conductive loop relative to the second adjacent conductive loop.

11. The body-mountable device of claim 7, wherein the first and second polymer layers in each conductive loop comprise paralyene.

12. The body-mountable device of claim 1, further comprising one or more spacers configured to maintain substantially uniform spacings between adjacent conductive loops in the plurality of conductive loops.

13. The body-mountable device of claim 12, wherein the one or more spacers comprise a polymeric material.

14. The body-mountable device of claim 12, wherein the one or more spacers comprise a metal.

15. The body-mountable device of claim 12, wherein the one or more spacers comprise one spacer positioned on the structure substantially opposite of the sensor.

16. The body-mountable device of claim 12, wherein the one or more spacers are positioned on the structure at a predetermined rotational orientation.

* * * * *